US011284791B2

(12) United States Patent
Tanabe et al.

(10) Patent No.: US 11,284,791 B2
(45) Date of Patent: Mar. 29, 2022

(54) IMAGE PROCESSING METHOD, PROGRAM, AND IMAGE PROCESSING DEVICE

(71) Applicant: NIKON CORPORATION, Tokyo (JP)

(72) Inventors: Yasushi Tanabe, Fujisawa (JP); Tomoharu Fujiwara, Gyoda (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 17/071,526

(22) Filed: Oct. 15, 2020

(65) Prior Publication Data
US 2021/0022600 A1 Jan. 28, 2021

Related U.S. Application Data

(63) Continuation of application No. PCT/JP2019/016654, filed on Apr. 18, 2019.

(30) Foreign Application Priority Data

Apr. 18, 2018 (JP) .............................. JP2018-080275

(51) Int. Cl.
*A61B 3/00* (2006.01)
*G06T 7/62* (2017.01)
(Continued)

(52) U.S. Cl.
CPC .............. *A61B 3/0058* (2013.01); *G06T 7/62* (2017.01); *G06T 7/70* (2017.01); *G06T 11/206* (2013.01);
(Continued)

(58) Field of Classification Search
CPC ........ A61B 3/0058; A61B 3/1241; G06T 7/62; G06T 7/70; G06T 11/206; G06T 11/60;
(Continued)

(56) References Cited

U.S. PATENT DOCUMENTS

2016/0135683 A1   5/2016   Yasuno

FOREIGN PATENT DOCUMENTS

JP   2008-229157 A   10/2008
JP   2015-000131 A   1/2015

OTHER PUBLICATIONS

International Search Report (PCT/ISA/210) dated Jul. 23, 2019, by the Japan Patent Office as the International Searching Authority for International Application No. PCT/JP2019/016654 and English translation. (Year: 2019).*

(Continued)

*Primary Examiner* — Jeffery A Brier
(74) *Attorney, Agent, or Firm* — Foley & Lardner LLP

(57) ABSTRACT

A visualization of choroidal blood vessel size is created. A vortex vein position is detected from a choroidal vascular image in which choroidal blood vessels have been visualized. Image processing is employed on the choroidal vascular image to extract first size choroidal blood vessels of a first size and to extract second size choroidal blood vessels of a second size different to the first size from the choroidal vascular image. A size analysis fundus image is generated in which a rectangular frame indicating the vortex vein position is displayed superimposed on the choroidal vascular image, and in which the first size choroidal blood vessels are displayed in red and the second size choroidal blood vessels are displayed in blue.

17 Claims, 22 Drawing Sheets

(51) Int. Cl.
  *G06T 7/70*   (2017.01)
  *G06T 11/20*  (2006.01)
  *G06T 11/60*  (2006.01)
  *G06T 7/00*   (2017.01)
  *A61B 3/12*   (2006.01)

(52) U.S. Cl.
  CPC .......... *G06T 11/60* (2013.01); *G06T 2200/24* (2013.01); *G06T 2207/10101* (2013.01); *G06T 2207/20101* (2013.01); *G06T 2207/30041* (2013.01); *G06T 2207/30101* (2013.01)

(58) Field of Classification Search
  CPC ....... G06T 2200/24; G06T 2207/10101; G06T 2207/20101; G06T 2207/30041; G06T 2207/30101; G06T 7/0012
  See application file for complete search history.

(56) References Cited

OTHER PUBLICATIONS

Written Opinion (PCT/ISA/237) dated Jul. 23, 2019, by the Japan Patent Office as the International Searching Authority for International Application No. PCT/JP2019/016654 and English translation. (Year: 2019).*

International Preliminary Report (PCT/ISA/373) dated Oct. 20, 2020, by The International Bureau of WIPO for International Application No. PCT/JP2019/016654 and English translation. (Year: 2020).*

Moriyama et al., "Detection of posterior vortex veins in eyes with pathologic myopia by ultra-widefield indocyanine green angiography", British Journal of Ophthalmology, Sep. 2017, vol. 101, issue 9, pp. 1179-1184.

* cited by examiner

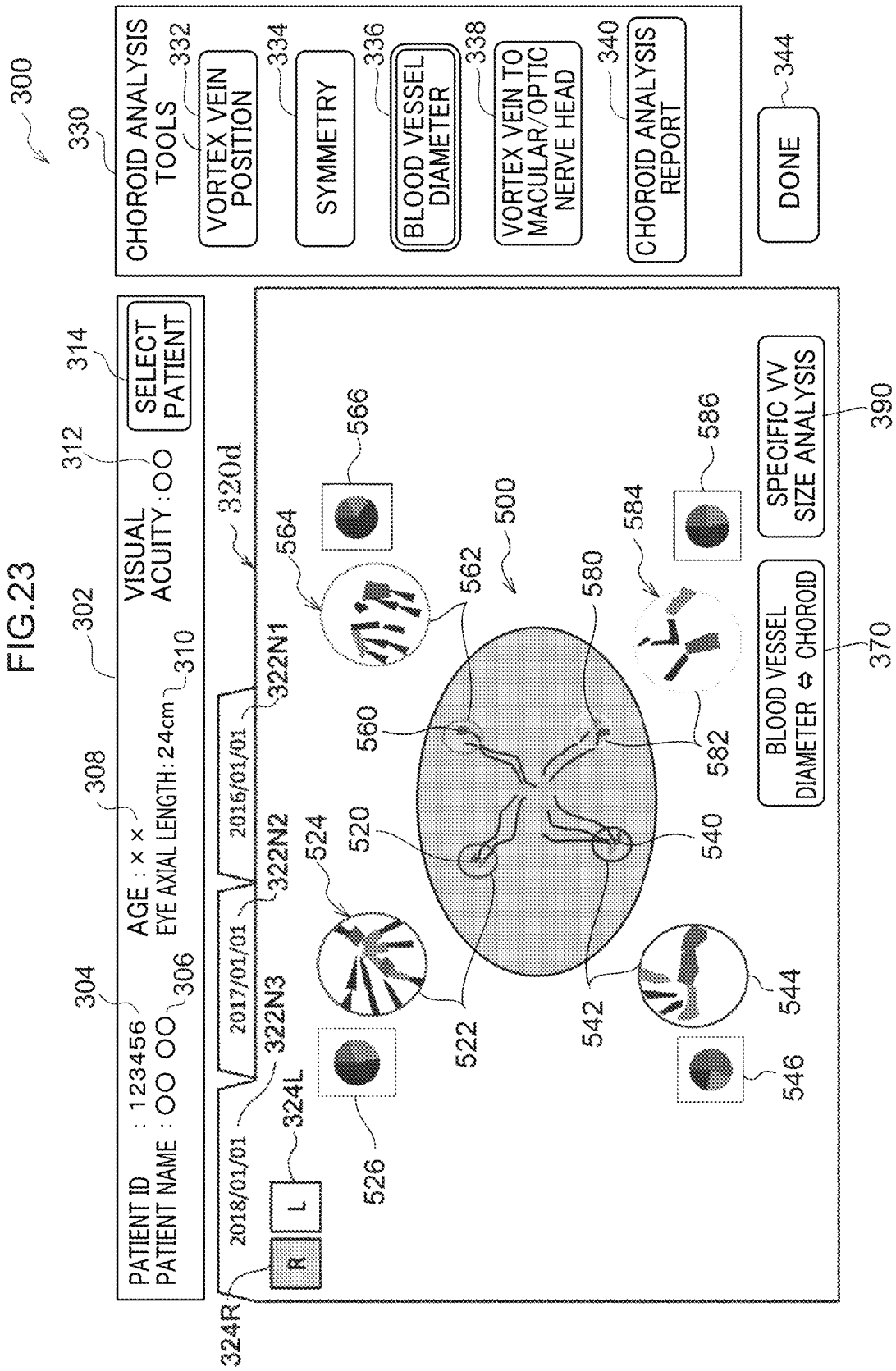

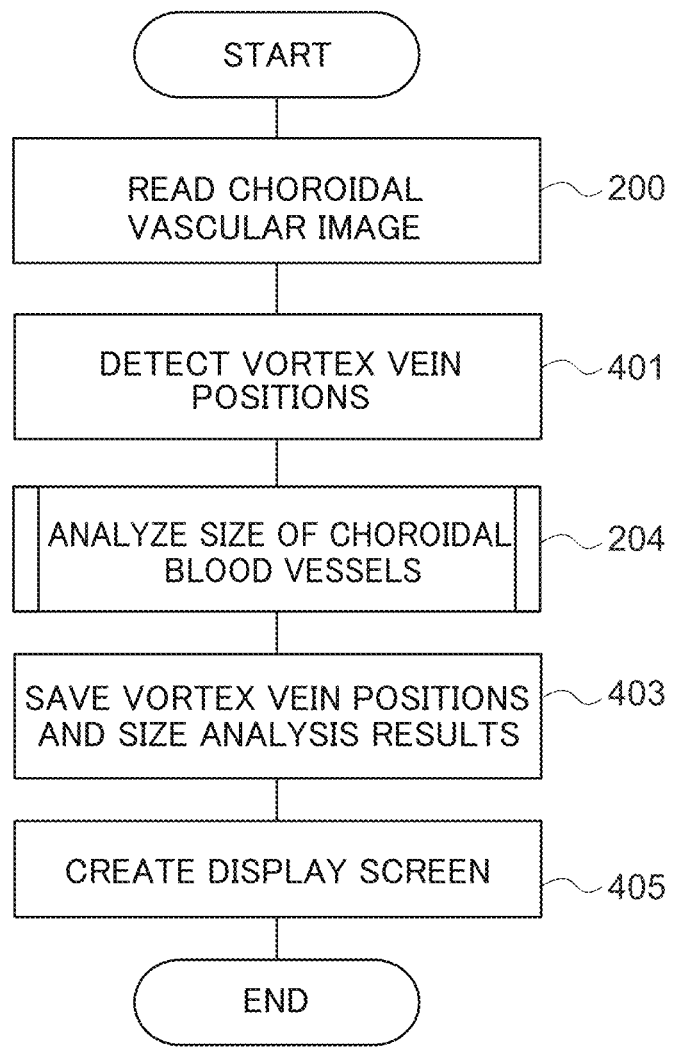

IMAGE PROCESSING METHOD, PROGRAM, AND IMAGE PROCESSING DEVICE

CROSS-REFERENCE TO RELATED APPLICATIONS

This application is a continuation application of International Application No. PCT/JP2019/016654 filed Apr. 18, 2019, the disclosure of which is incorporated herein by reference in its entirety. Further, this application claims priority from Japanese Patent Application No. 2018-080275, filed Apr. 18, 2018, the disclosure of which is incorporated herein by reference in their entirety.

TECHNICAL FIELD

Technology disclosed herein relates to an image processing method, a program, and an image processing device.

RELATED ART

Technology is disclosed in Japanese Patent Application Laid-Open (JP-A) No. 2015-131 for quantification of a choroid vascular plexus from measurement data of optical coherence tomography (hereafter referred to as OCT).

SUMMARY

An image processing method of a first aspect of technology disclosed herein includes detecting a vortex vein position from a fundus image in which choroidal blood vessels have been visualized, employing image processing on the fundus image to extract first size choroidal blood vessels of a first size and to extract second size choroidal blood vessels of a second size different to the first size, and displaying a position display image indicating the vortex vein position displayed superimposed on the fundus image, and generating a size analysis fundus image to display the first size choroidal blood vessels with a first display method and to display the second size choroidal blood vessels with a second display method different to the first display method.

An image processing method of a second aspect of technology disclosed herein includes detecting a vortex vein position from a fundus image in which choroidal blood vessels have been visualized, detecting intersection points between choroidal blood vessels and a circle centered on the vortex vein position, identifying a size of the choroidal blood vessels at the intersection points, and creating a graph indicating a relationship to the size of the choroidal blood vessel at the intersection point.

An image processing method of a third aspect of technology disclosed herein includes detecting a vortex vein position from a fundus image in which choroidal blood vessels have been visualized, detecting intersection points between choroidal blood vessels and a circle centered on the vortex vein position, identifying a blood vessel diameter of the choroidal blood vessels at the intersection points, and creating a histogram of a number of the choroidal blood vessels against the blood vessel diameter.

A program of a fourth aspect of technology disclosed herein causes the image processing method of any one of the first aspect to the third aspect to be executed by a computer.

An image processing device of a fifth aspect of technology disclosed herein includes a storage device configured to store a program to cause an image processing method to be executed by a processing device, a processing device configured to execute the image processing method by executing the program stored in the storage device. The image processing method is the image processing method of any one of the first aspect to the third aspect.

An image processing method of a sixth aspect of technology disclosed herein includes detecting a vortex vein position from a fundus image in which choroidal blood vessels have been visualized, analyzing a size of the choroidal blood vessels in the fundus image, and creating a display screen indicating a relationship between the vortex vein position and size of the choroidal blood vessel.

BRIEF DESCRIPTION OF DRAWINGS

FIG. 23 is a diagram illustrating a display screen combining blood vessel diameter analysis results with VV position analysis results.

FIG. 24 is a flowchart of an image processing program.

DETAILED DESCRIPTION

Detailed explanation follows regarding an exemplary embodiment in the present invention, with reference to the drawings. In the following, for ease of explanation, a scanning laser ophthalmoscope is referred to as an "SLO".

Figure 1:
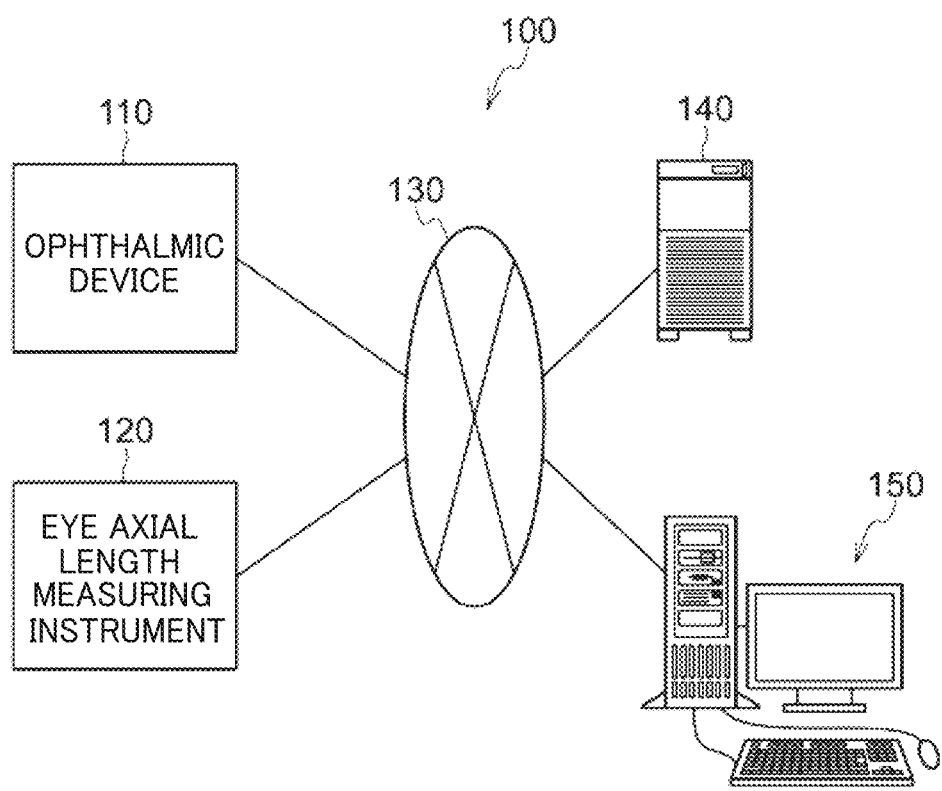
FIG. 1 is a block diagram illustrating an ophthalmic system 100.

The configuration of an ophthalmic system 100 will now be described with reference to FIG. 1. As illustrated in FIG. 1, the ophthalmic system 100 includes an ophthalmic device 110, an eye axial length measuring instrument 120, a management server device (hereinafter referred to as "management server") 140, and an image display device (hereinafter referred to as "image viewer") 150. The ophthalmic device 110 acquires fundus images. The eye axial length measuring instrument 120 measures the axial length of patient eyes. The management server 140 stores plural fundus images and eye axial lengths obtained by imaging the fundi of plural patients using the ophthalmic device 110, stored associated with respective patient IDs. The image viewer 150 displays fundus images acquired by the management server 140.

The ophthalmic device 110, the eye axial length measuring instrument 120, the management server 140, and the image viewer 150 are connected to each other over a network 130.

Note that other ophthalmic instruments (instruments for performing examinations such as optical coherence tomography (OCT) measurement, field of view measurement, and intraocular pressure measurement) and a diagnostic support device that performs image analysis using artificial intelligence may be connected over the network 130 to the ophthalmic device 110, the eye axial length measuring instrument 120, the management server 140, and the image viewer 150.

Figure 2:
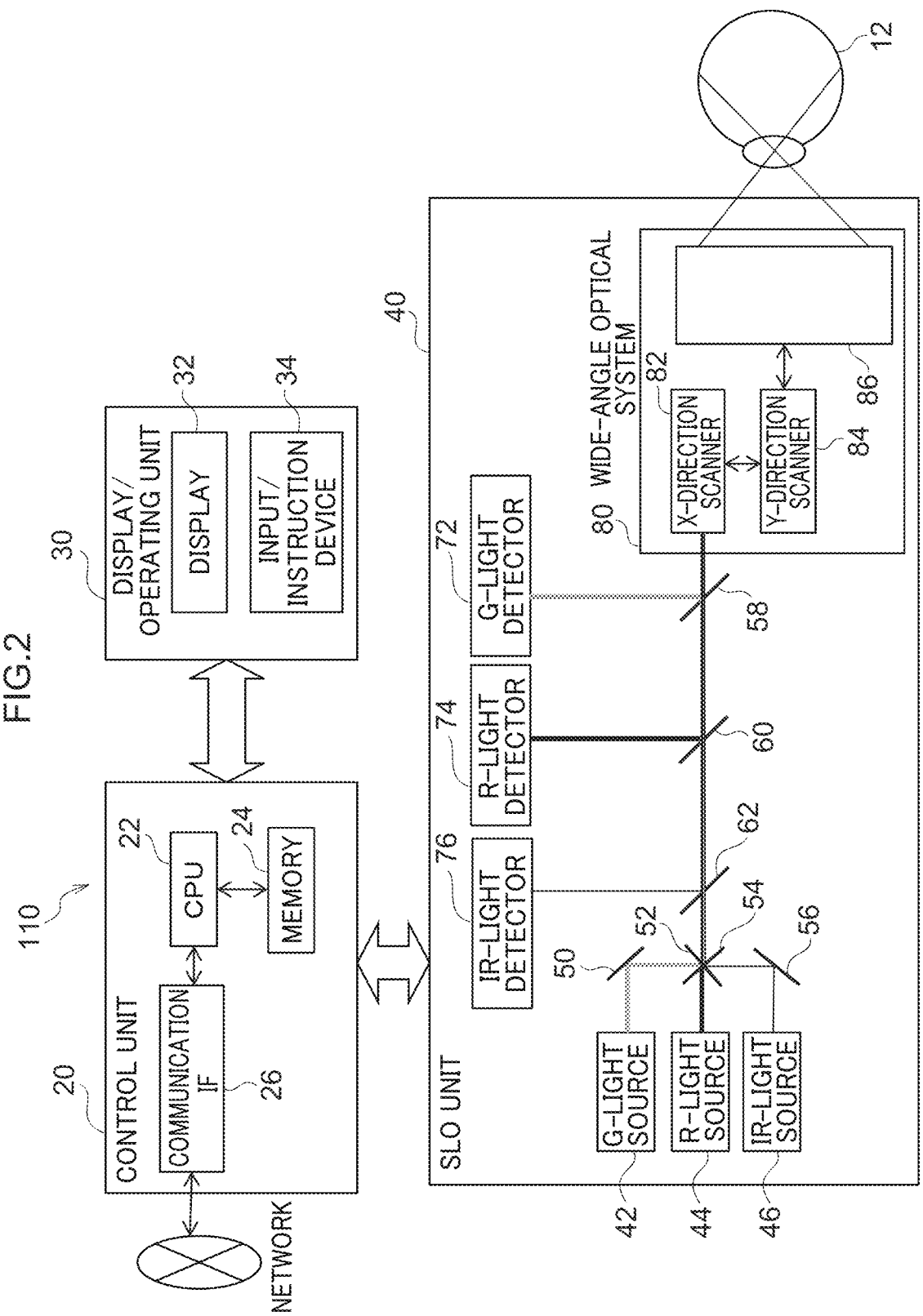
FIG. 2 is a schematic configuration diagram illustrating an overall configuration of an ophthalmic device 110.

Explanation follows regarding a configuration of the ophthalmic device 110, with reference to FIG. 2. As illustrated in FIG. 2, the ophthalmic device 110 includes a control unit 20, a display/operation unit 30, and an SLO unit 40, and images the posterior segment (fundus) of the examined eye 12. Furthermore, a non-illustrated OCT unit may be provided for acquiring OCT data of the fundus.

The control unit 20 includes a CPU 22, memory 24, a communication interface (I/F) 26, and the like. The display/operation unit 30 is a graphical user interface to display images obtained by imaging, and to receive various instructions including an imaging instruction. The display/operation unit 30 also includes a display 32 and an input/instruction device 34 such as a touch panel.

The SLO unit 40 includes a light source 42 for green light (G-light: wavelength 530 nm), a light source 44 for red light (R-light: wavelength 650 nm), and a light source 46 for infrared radiation (IR-light (near-infrared light): wavelength 800 nm). The light sources 42, 44, 46 respectively emit light as commanded by the control unit 20. The SLO unit 40 includes optical systems 50, 52, 54 and 56 that reflect or transmit light from the light sources 42, 44 and 46 in order to guide the reflected light into a single optical path. The optical systems 50 and 56 are mirrors, and the optical systems 52 and 54 are beam splitters. The G-light is reflected by the optical systems 50 and 54, the R-light is transmitted through the optical systems 52 and 54, and the IR-light is reflected by the optical systems 52 and 56, such that all are guided into a single optical path.

The SLO unit 40 includes a wide-angle optical system 80 for two-dimensionally scanning light from the light sources 42, 44, 46 across the posterior segment (fundus) of the examined eye 12. The SLO unit 40 includes a beam splitter 58 that, from out of the light from the posterior segment (fundus) of the examined eye 12, reflects the G-light and transmits light other than the G-light. The SLO unit 40 includes a beam splitter 60 that, from out of the light transmitted through the beam splitter 58, reflects the R-light and transmits light other than the R-light. The SLO unit 40 includes a beam splitter 62 that, from out of the light that has transmitted through the beam splitter 60, reflects IR-light. The SLO unit 40 is provided with a G-light detection element 72 that detects the G-light reflected by the beam splitter 58, an R-light detection element 74 that detects the R-light reflected by the beam splitter 60, and an IR-light detection element 76 that detects IR-light reflected by the beam splitter 62.

The wide-angle optical system 80 includes an X-direction scanning device 82 configured by a polygon mirror to scan the light from the light sources 42, 44, 46 in an X direction, a Y-direction scanning device 84 configured by a galvanometer mirror to scan the light from the light sources 42, 44, 46 in a Y direction, and an optical system 86 including a non-illustrated slit mirror and elliptical mirror to widen the angle over which the light is scanned. The optical system 86 is capable of achieving a field of view (FOV) of the fundus with a larger angle than in conventional technology, enabling a fundus region to be imaged over a wider range than when employing conventional technology. More specifically, a fundus region can be imaged over a wide range of approximately 120 degrees of external light illumination angles from outside the examined eye 12 (approximately 200 degrees about a center O of the eyeball of the examined eye 12 as a reference position for an internal light illumination angle capable of being imaged in practice by illuminating the fundus of the examined eye 12 with scanning light). The optical system 86 may be configured employing plural lens sets instead of a slit mirror and elliptical mirror. The X-direction scanning device 82 and the Y-direction scanning device 84 may also be scanning devices employing two-dimensional scanners configured by MEMS mirrors.

A configuration may employ a system using an elliptical mirror as described in International Applications PCT/JP2014/084619 or PCT/JP2014/084630 in cases in which a system including a slit mirror and an elliptical mirror is used as the optical system 86. The respective disclosures of International Application PCT/JP2014/084619 (International Publication WO2016/103484) filed on Dec. 26, 2014 and International Application PCT/JP2014/084630 (International Publication WO2016/103489) filed on Dec. 26, 2014 are incorporated by reference herein in their entireties.

Note that when the ophthalmic device 110 is installed on a horizontal plane, the "X direction" corresponds to a horizontal direction and the "Y direction" corresponds to a direction perpendicular to the horizontal plane. A direction joining the center of the pupil of the anterior eye portion of the examined eye 12 and the center of the eyeball is referred to as the "Z direction". The X direction, the Y direction, and the Z direction are accordingly perpendicular to one another.

A color fundus image is obtained by imaging the fundus of the examined eye 12 simultaneously with G-light and R-light. More specifically, the control unit 20 controls the light sources 42, 44 such that the light sources 42, 44 emit light at the same time, and scans the G-light and R-light across the fundus of the examined eye 12 using the wide-angle optical system 80. G-light reflected from the fundus of the examined eye 12 is detected by the G-light detection element 72, and image data of a second fundus image (a G fundus image) is generated by the CPU 22 of the ophthalmic device 110. Similarly, R-light reflected from the fundus of the examined eye 12 is detected by the R-light detection element 74, and image data of a first fundus image (R fundus image) is generated by the CPU 22 of the ophthalmic device 110. In cases in which IR-light is illuminated, IR-light reflected from the fundus of the examined eye 12 is detected by the IR-light detection element 76, and image data of an IR fundus image is generated by the CPU 22 of the ophthalmic device 110.

The structure of the eye is configured by the vitreous body covered by plural layers that each have a different structure. These plural layers include the retina, the choroid, and the sclera in sequence from the side closest to the vitreous body outward. R-light passes through the retina and travels as far as the choroid. Accordingly, the first fundus image (R fundus image) includes information relating to blood vessels present in the retina (retinal blood vessels) and information relating to blood vessels present in the choroid (choroidal blood vessels). By contrast, G-light only travels as far as the retina. Accordingly, the second fundus image (G fundus image) includes information relating to the blood vessels (retinal blood vessels) present in the retina.

The CPU 22 of the ophthalmic device 110 mixes the first fundus image (R fundus image) and the second fundus image (G fundus image) together at a specific ratio, and displays the resulting color fundus image on the display 32. Note that a configuration may be adopted in which instead of the color fundus image, the first fundus image (R fundus image), the second fundus image (G fundus image), or an IR fundus image is displayed.

Image data of the first fundus image (R fundus image), image data of the second fundus image (G fundus image), and image data of the IR fundus image is sent from the ophthalmic device 110 to the management server 140 through the communication IF 26.

The fundus of the examined eye 12 is accordingly imaged by the G-light and R-light at the same time, and so each of the positions on the first fundus image (R fundus image) and the positions on the second fundus image (G fundus image) corresponding to these respective positions, are the same positions on the fundus.

The eye axial length measuring instrument 120 in FIG. 1 has two modes for measuring the eye axial length, this being the length of the examined eye 12 in an eye axial direction (Z direction), namely a first mode and a second mode. In the first mode, light from a non-illustrated light source is guided into the examined eye 12, and interference light generated from interference between reflected light from the fundus and reflected light from the cornea is received, and the eye axial length is measured based on an interference signal represented by the interference light received. The second mode is a mode in which non-illustrated ultrasound waves are employed to measure the eye axial length. The eye axial length measuring instrument 120 transmits the eye axial length measured using either the first mode or the second mode to the management server 140. The eye axial length may be measured using both the first mode and the second mode, in which case an average of the eye axial lengths measured by the two modes is transmitted to the management server 140 as the eye axial length.

As one item of data about a patient, the eye axial length is saved as patient information in the management server 140, and is also utilized in fundus image analysis.

Figure 3:
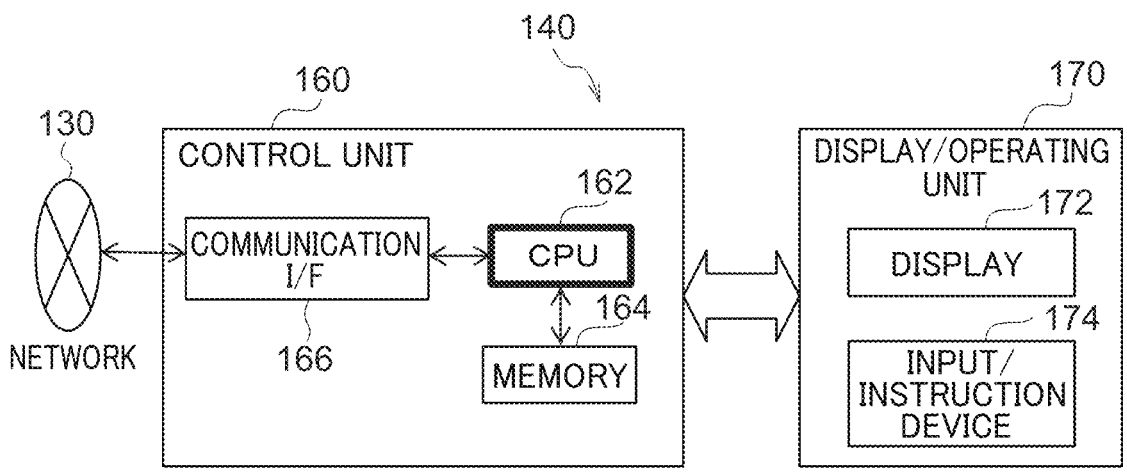
FIG. 3 is a block diagram of a configuration of an electrical system of a management server 140.

Next, a configuration of the management server 140 will be described with reference to FIG. 3. As illustrated in FIG. 3, the management server 140 includes a control unit 160, and a display/operation unit 170. The control unit 160 is equipped with a computer including a CPU 162, memory 164 configured by a storage device, a communication interface (I/F) 166, and the like. Note that an image processing program is stored in the memory 164. The display/operation unit 170 is a graphical user interface for displaying images and for receiving various instructions. The display/operation unit 170 includes a display 172 and a touch panel 174.

The configuration of the image viewer 150 is similar to that of the management server 140, and so description thereof is omitted.

Figure 4:
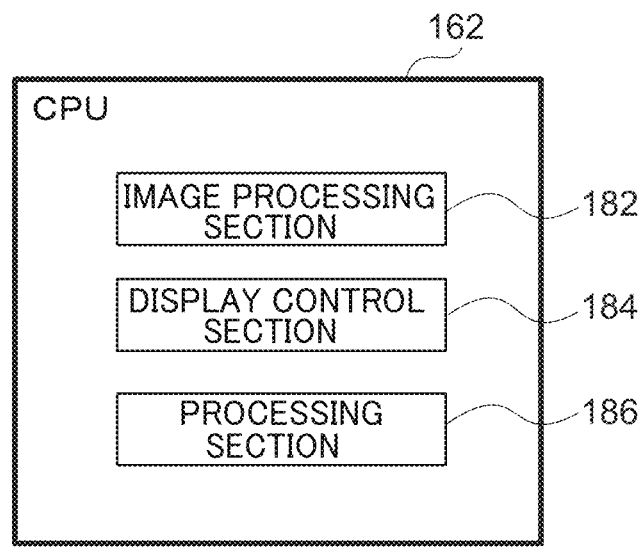
FIG. 4 is a block diagram illustrating functions of a CPU 162 of a management server 140.

Next, with reference to FIG. 4, description follows regarding each of various functions implemented by the CPU 162 of the management server 140 executing the image processing program. The image processing program includes an image processing function, a display control function, and a processing function. By the CPU 162 executing the image processing program including each of these functions, the CPU 162 functions as an image processing section 182, a display control section 184, and a processing section 186, as illustrated in FIG. 4.

Figure 5:
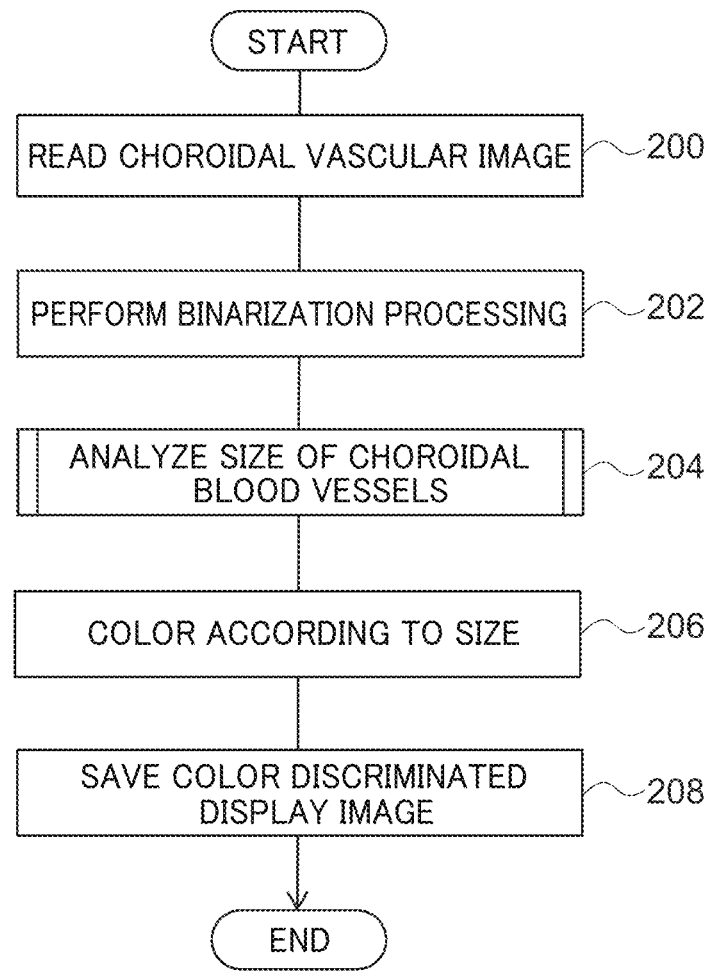
FIG. 5 is flowchart of an image processing program of a first exemplary embodiment.

Next, with reference to FIG. 5, detailed description follows regarding image processing by the management server 140. The image processing (image processing method) illustrated in the flowchart of FIG. 5 is implemented by the CPU 162 of the management server 140 executing the image processing program.

The image processing program is executed by the management server 140 when generating a choroidal vascular image based on a fundus image that is a fundus image received from the ophthalmic device 110.

Figure 6:
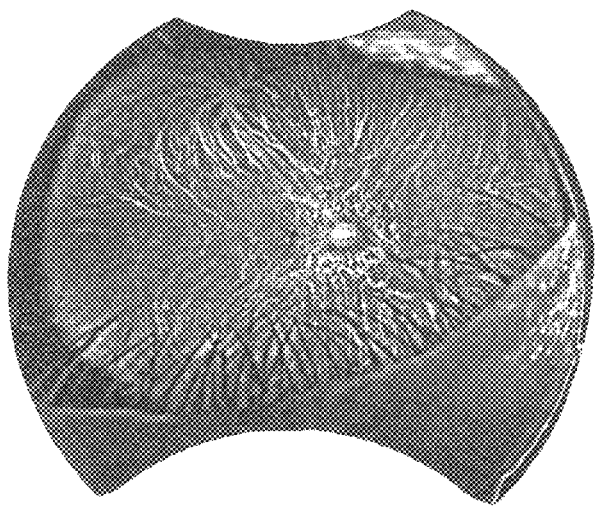
FIG. 6 is a diagram illustrating a choroidal vascular image.

Note that a choroidal vascular image is generated in the following manner. The image processing section 182 of the management server 140 subjects the second fundus image (G fundus image) to black hat filter processing so as to extract the retinal blood vessels from the second fundus image (G fundus image). Next, the image processing section 182 removes the retinal blood vessels from the first fundus image (R fundus image) by performing in-painting processing employing the retinal blood vessels extracted from the second fundus image (G fundus image). Namely, processing is performed that uses position information relating to the retinal blood vessels extracted from the second fundus image (G fundus image) to infill the retinal blood vessel structure of the first fundus image (R fundus image) with the same values to those of surrounding pixels. The image processing section 182 then subjects the image data of the first fundus image (R fundus image) from which the retinal blood vessels have been removed to contrast-limited adaptive histogram equalization, thereby emphasizing the choroidal blood vessels in the first fundus image (R fundus image). A choroidal vascular image as illustrated in FIG. 6 is obtained thereby. The generated choroidal vascular image is stored in the memory 164. The generated choroidal vascular image is stored in the memory 164.

Moreover, although the choroidal vascular image is generated from the first fundus image (R fundus image) and the second fundus image (G fundus image), the image processing section 182 may next generate a choroidal vascular image employing the first fundus image (R fundus image) or the IR fundus image imaged with IR light. Regarding the method used to generate the choroidal fundus image, the disclosure of Japanese Patent Application No. 2018-052246, filed on Mar. 20, 2018, is incorporated in its entirety by reference herein.

When the image processing program is started, at step 200 of FIG. 5, the processing section 186 reads the choroidal vascular image (see FIG. 6) from the memory 164.

Figure 7:
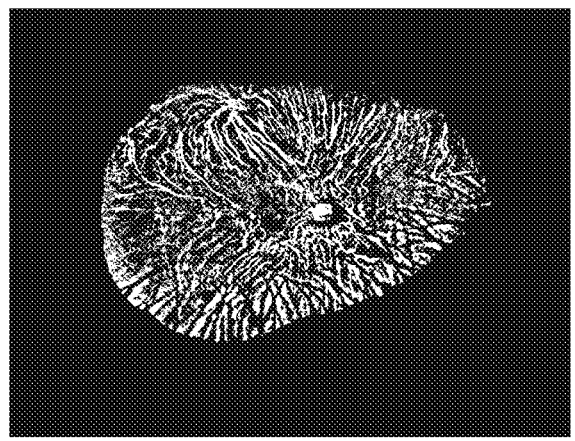
FIG. 7 is a diagram illustrating a binary image of a choroidal vascular image.

At step 202, the image processing section 182 crops the choroidal vascular image to a fundus region (removing eyelids etc.) and subjects the fundus region to binarization processing so as to generate a binary image (see FIG. 7).

At step 204, the image processing section 182 executes size analysis processing to analyze the size of choroidal blood vessels that appear as white in the binary image. The size analysis processing generates a first size blood vessel image in which only first size blood vessels of a size of t3 (µm) or greater are extracted, a second size blood vessel image in which only second size blood vessels of a size of from t2 (µm) up to but not including t3 (µm) are extracted, and a third size blood vessel image in which only third size blood vessels of a size of from t1 (µm) up to but not including t2 (µm) are extracted. In this example t1 is 160 µm, t2 is 320 µm, and t3 is 480 µm.

Note that 160 µm for t1 and 320 µm for t2 are values for classifying blood vessels by size. However these are merely examples thereof, and other values may be employed therefor.

Details regarding the blood vessel size analysis processing are described later.

At step image processing control section 206, the display control section 184 generates three images, with vascular portions of the first size blood vessel image colored red, with vascular portions of the second size blood vessel image colored green, and with vascular portions of the third size blood vessel image colored blue. Furthermore, these three blood vessel images are combined to generate a colored choroidal vascular image colored according to size. Although in this example the vascular portions of the first size blood vessel image, the vascular portions of the second size blood vessel image, and the vascular portions of the third size blood vessel image, are respectively colored red, green, and blue, other respective colors may be employed therefor.

At step 208, the processing section 186 saves each of the various images generated at step 206 in the memory 164.

Figure 8:
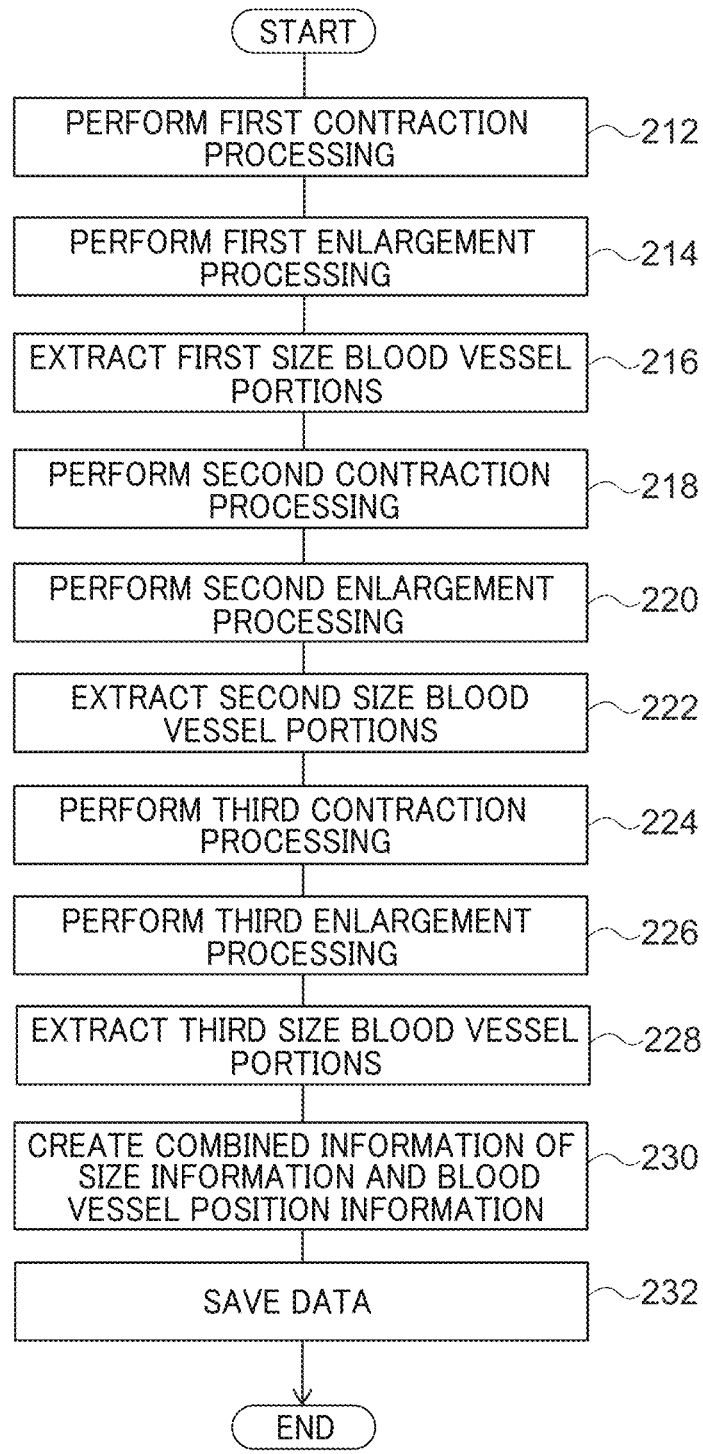
FIG. 8 is a flowchart of a choroidal blood vessel size analysis processing program at step 204 of FIG. 5.

Next, description follows regarding choroidal blood vessel size analysis processing of step 204 executed by the image processing section 182 of the management server 140, with reference to FIG. 8.

Figure 9A:
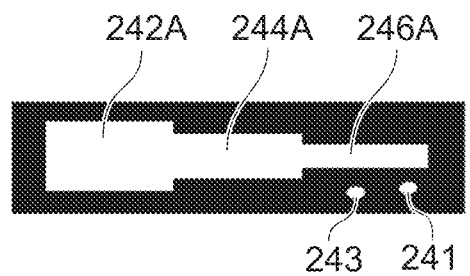
FIG. 9A is an explanatory diagram to explain choroidal blood vessel size analysis processing.

At step 212, the image processing section 182 performs first contraction processing on the generated binary image (see FIG. 7). FIG. 9A is a diagram in which part of a choroidal blood vessel is displayed schematically, and is a diagram in which blood vessel 242A, 244A, 246A of three size types, these being a first size (pixel number of 7 pixels), a second size (pixel number of 5 pixels), and a third size (pixel number of 3 pixels), and noise 241, 243 at two locations having a size of 1 pixel, are displayed in white.

Figure 9B:
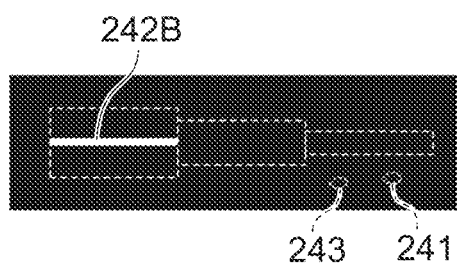
FIG. 9B is an explanatory diagram to explain choroidal blood vessel size analysis processing.
Figure 9C:
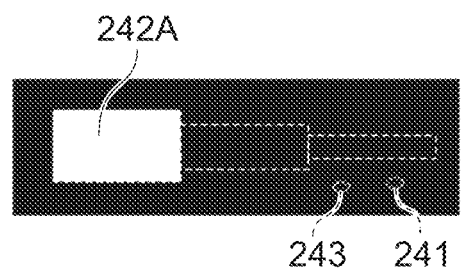
FIG. 9C is an explanatory diagram to explain choroidal blood vessel size analysis processing.
Figure 9D:
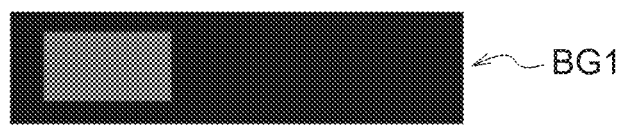
FIG. 9D is an explanatory diagram to explain choroidal blood vessel size analysis processing.

When first contraction processing is executed on FIG. 9A (by changing white pixels into black pixels) to contract 3 pixels inward from the edges of the white portions, white remains at a portion 242B of the first size blood vessel 242A and the other white portions are erased, as illustrated in FIG. 9B. Then at step 214, the image processing section 182 performs first enlargement processing on the binary image that has been subjected to the first contraction processing (on FIG. 9B). In the first enlargement processing, processing is performed to enlarge by 3 white pixels from any white portions outward (by changing black pixels into white pixels). This processing results in only the first size blood vessel 242A being reproduced, as illustrated in FIG. 9C. Then at step 216, by applying red to the first size blood vessel 242A portion, the image processing section 182 generates a first size blood vessel image BG1 in red from which the noise 241, 243 has been removed, as in FIG. 9D.

Figure 9E:
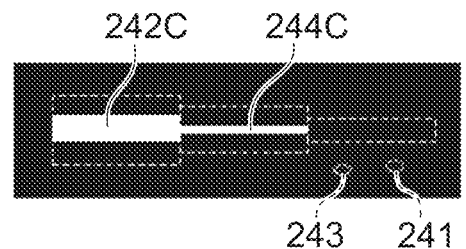
FIG. 9E is an explanatory diagram to explain choroidal blood vessel size analysis processing.
Figure 9F:
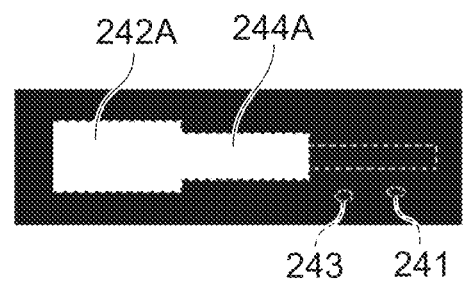
FIG. 9F is an explanatory diagram to explain choroidal blood vessel size analysis processing.
Figure 9G:
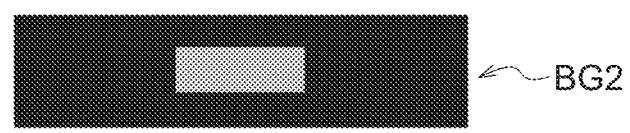
FIG. 9G is an explanatory diagram to explain choroidal blood vessel size analysis processing.

At step 218, the image processing section 182 performs second contraction processing on the generated binary image (see FIG. 7). When the second contraction processing is executed on FIG. 9A (by changing white pixels into black pixels) to contract 2 pixels inward from the edges of the white portions, white remains at portions 242C, 244C of the first size blood vessel 242A and the second size blood vessel 244A and the other white portions are erased, as illustrated in FIG. 9E. Next at step 220, the image processing section 182 performs second enlargement processing on the binary image that has been subjected to the second contraction processing (on FIG. 9E). In the second enlargement processing, processing is performed to enlarge by 2 white pixels from any white portion outward. This processing results in only the first size blood vessel 242A and the second size blood vessel 244A being reproduced, as illustrated in FIG. 9F. Then at step 222, the image processing section 182 applies green to a portion remaining after taking the difference between the binary image after the second enlargement processing (FIG. 9F) and the binary image after the first enlargement processing (FIG. 9C). A second size blood vessel image BG2 in green is accordingly generated thereby from which noise has been removed, as illustrated in FIG. 9G.

Figure 9H:
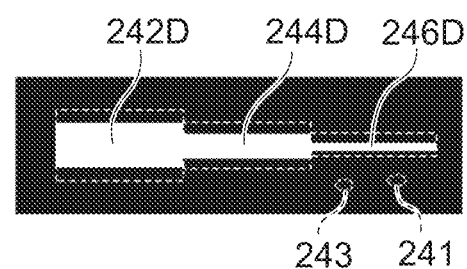
FIG. 9H is an explanatory diagram to explain choroidal blood vessel size analysis processing.
Figure 9I:
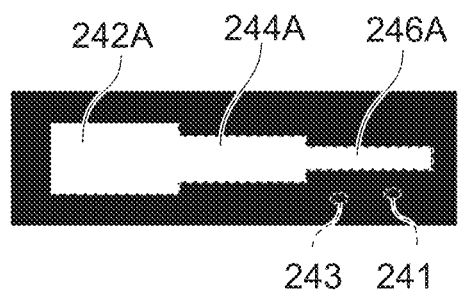
FIG. 9I is an explanatory diagram to explain choroidal blood vessel size analysis processing.
Figure 9J:
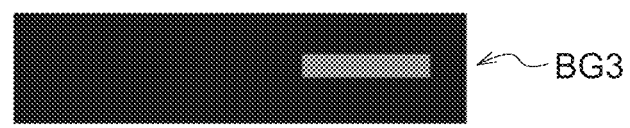
FIG. 9J is an explanatory diagram to explain choroidal blood vessel size analysis processing.

At step 224, the image processing section 182 performs third contraction processing on the generated binary image (see FIG. 7). When the third contraction processing is executed on FIG. 9A (by changing white pixels into black pixels) to contract 1 pixel inward from the edges of the white portions, portions 242D, 244D, 246D of the first size blood vessel 242A, the second size blood vessel 244A, and the third size blood vessel 246A, and portions of noise remain white and the other white portions are erased, as illustrated in FIG. 9H. Next, at step 226, the image processing section 182 performs third enlargement processing on the binary image that has been subjected to the third contraction processing (FIG. 9H). In the third enlargement processing, processing is performed to enlarge by 1 white pixel from any white portion outward. This processing results in the first size blood vessel, the second size blood vessel, and the third size blood vessel being reproduced, as illustrated in FIG. 9I. Then at step 228, blue is applied to a portion remaining after taking the difference between the binary image after the third enlargement processing (FIG. 9I) and the binary image after the second enlargement processing (FIG. 9F). A third size blood vessel image BG3 in blue is accordingly generated thereby from which the noise has been removed, as illustrated in FIG. 9J.

At step 230, the image processing section 182 extracts the first size blood vessel positions from the first size blood vessel image BG1, extracts the second size blood vessel positions from the second size blood vessel image BG2, and extracts the third size blood vessel positions from the third size blood vessel image BG3, then creates combined information combining size information and blood vessel position information.

At step 232, the image processing section 182 saves in the memory 164 the combined information combining size information and blood vessel position information, and the first size blood vessel image BG1, the second size blood vessel image BG2, and the third size blood vessel image BG3. The processing then proceeds to step 206 of FIG. 5.

Next, description follows regarding a display screen in the choroidal vascular analysis mode of the first exemplary embodiment. The management server 140 includes various following data for displaying a display screen of the choroidal vascular analysis mode.

First, as described above, image data for the fundus images (the first fundus image (R fundus image) and the second fundus image (G fundus image)) is transmitted from the ophthalmic device 110 to the management server 140, and the management server 140 holds the image data for the fundus images (the first fundus image (R fundus image) and the second fundus image (G fundus image)). The management server 140 also holds data about each of the choroidal blood vessels and about the color that is associated with each choroidal blood vessel according to the choroidal blood vessel size.

Moreover, personal information about a patient is also input to the ophthalmic device 110 when the fundus of the patient is being imaged. The personal information includes an ID, name, age, visual acuity, and the like of the patient. Moreover, information indicating whether the eye whose fundus is imaged is either the right eye or the left eye is also input when the fundus of the patient is being imaged. Furthermore, the imaging date/time is also input when the fundus of the patient is being imaged. Data for the personal information, right eye/left eye information, and imaging date/time is transmitted from the ophthalmic device 110 to the management server 140. The management server 140 holds the data for the personal information, right eye/left eye information, and imaging date/time. The management server 140 also holds data for the eye axial length.

Thus as described above, the management server 140 holds the above data (contents data) to display the choroidal vascular analysis mode display screen.

However, sometimes a doctor wants to diagnose the state of the choroidal blood vessels of a patient. In such cases the doctor uses the image viewer 150 to transmit a request to the management server 140 to generate a display screen for the choroidal vascular analysis mode display screen. On receipt of such an instruction, the management server 140 transmits data for the choroidal vascular analysis mode display screen to the image viewer 150. On receipt of the choroidal vascular analysis mode display screen data and based on the choroidal vascular analysis mode display screen data, the image viewer 150 displays the display screen 300 for the choroidal vascular analysis mode illustrated in FIG. 10 on a display 172 of the image viewer 150.

Figure 10:
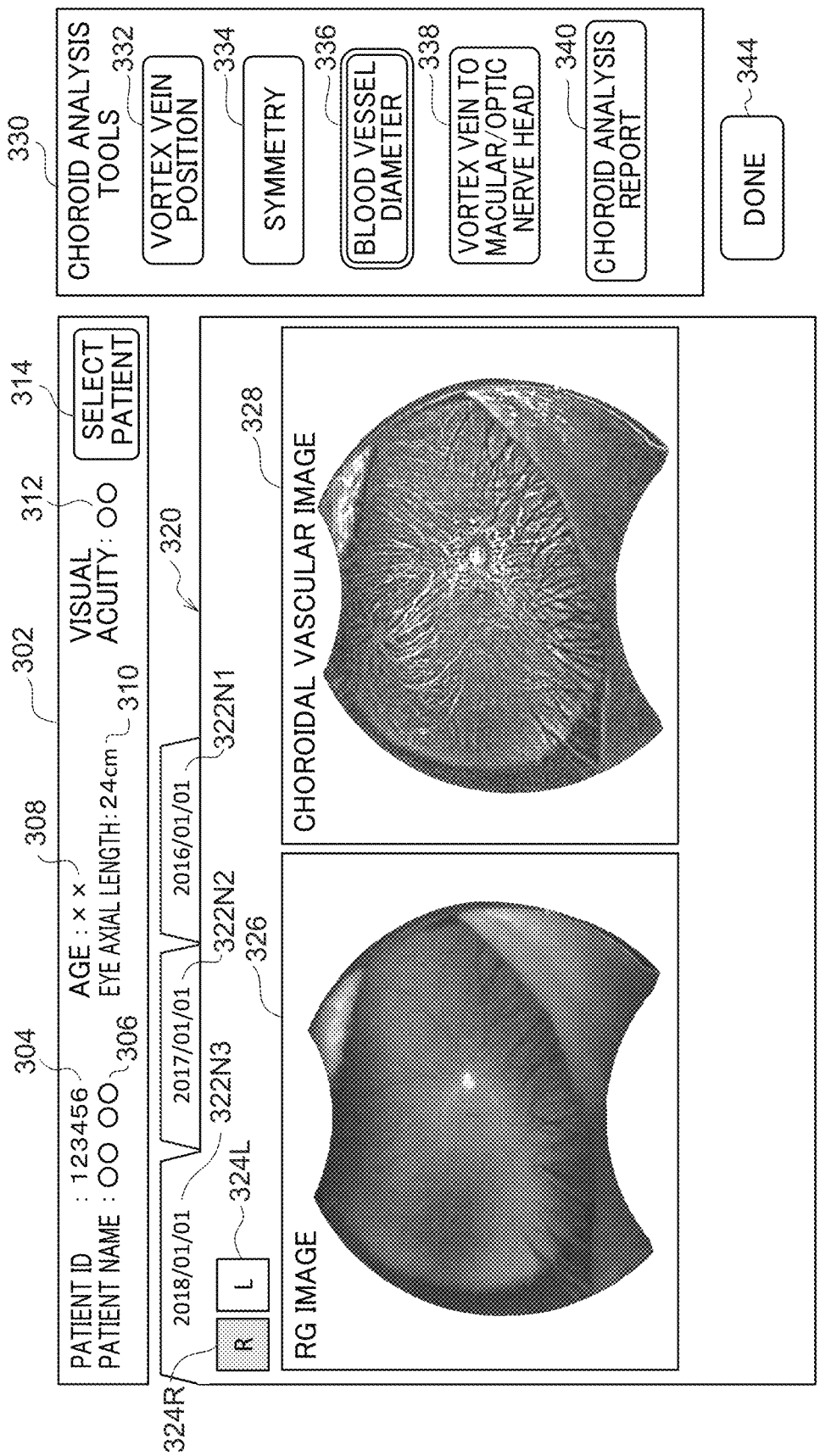
FIG. 10 is a diagram illustrating a display screen 300 for a choroidal vascular analysis mode.

Explanation follows regarding the choroidal vascular analysis mode display screen 300 illustrated in FIG. 10. As illustrated in FIG. 10, the choroidal vascular analysis mode display screen 300 includes a personal information display field 302 for displaying personal information about a patient, an image display field 320, and a choroid analysis tool display field 330.

The personal information display field 302 includes a patient ID display field 304, a patient name display field 306, an age display field 308, an eye axial length display field 310, a visual acuity display field 312, and a patient selection icon 314. Various information is displayed in the patient ID display field 304, the patient name display field 306, the age display field 308, the eye axial length display field 310, and the visual acuity display field 312. Note that when the patient selection icon 314 is clicked, a list of patients is displayed on the display 172 of the image viewer 150, so as to let a user (doctor) select the patient for analysis.

The image display field 320 includes imaging date display fields from 322N1 to 322N3, a right eye information display field 324R, a left eye information display field 324L, an RG image display field 326, a choroidal vascular image display field 328. The imaging date display fields from 322N1 to 322N3 correspond to imaging dates of Jan. 1, 2016, Jan. 1, 2017, and Jan. 1, 2018. Note that the RG image is an image obtained by combining the first fundus image (R fundus image) and the second fundus image (G fundus image) with the magnitudes of the respective pixel values combined at a specific ratio (for example, 1:1).

The choroid analysis tool display field 330 is a field displaying various types of icon for selecting plural choroid analysis tools. These include a vortex vein position icon 332, a symmetry icon 334, a blood vessel diameter icon 336, a vortex vein to macular/optic nerve head icon 338, and a choroid analysis report icon 340. The vortex vein position icon 332 instructs display of analysis results of vortex vein positions. The symmetry icon 334 instructs display of analysis results of fundus choroidal blood vessels symmetry. The blood vessel diameter icon 336 instructs display of analysis results related to the diameters of the choroidal blood vessels. The vortex vein to macular/optic nerve head icon 338 instructs display of analysis results of positions between the vortex vein, and the macular and optic nerve head. The choroid analysis report icon 340 instructs display of a choroid analysis report.

In the example illustrated in FIG. 10, an RG image and a choroidal vascular image are displayed for the fundus of the right eye (324R icon is illuminated) of a patient identified by the patient ID: 123456 as imaged on the imaging day corresponding to the imaging date display field when the imaging date display field 322N3 is clicked from out of the imaging date display fields 322N1 to 322N3.

Next, description follows regarding a first display embodiment of a choroidal vascular analysis mode display screen displayed on the image viewer 150. The image viewer 150 displays the choroidal vascular analysis mode display screen 300 illustrated in FIG. 10 on the display 172 of the image viewer 150. When the blood vessel diameter icon 336 is clicked in the choroid analysis tool display field 330 of FIG. 10, display changes to a blood vessel diameter display screen illustrated in FIG. 11 (the image display field 320 of FIG. 10 changes to the blood vessel diameter display screen 320a of FIG. 11).

Figure 11:
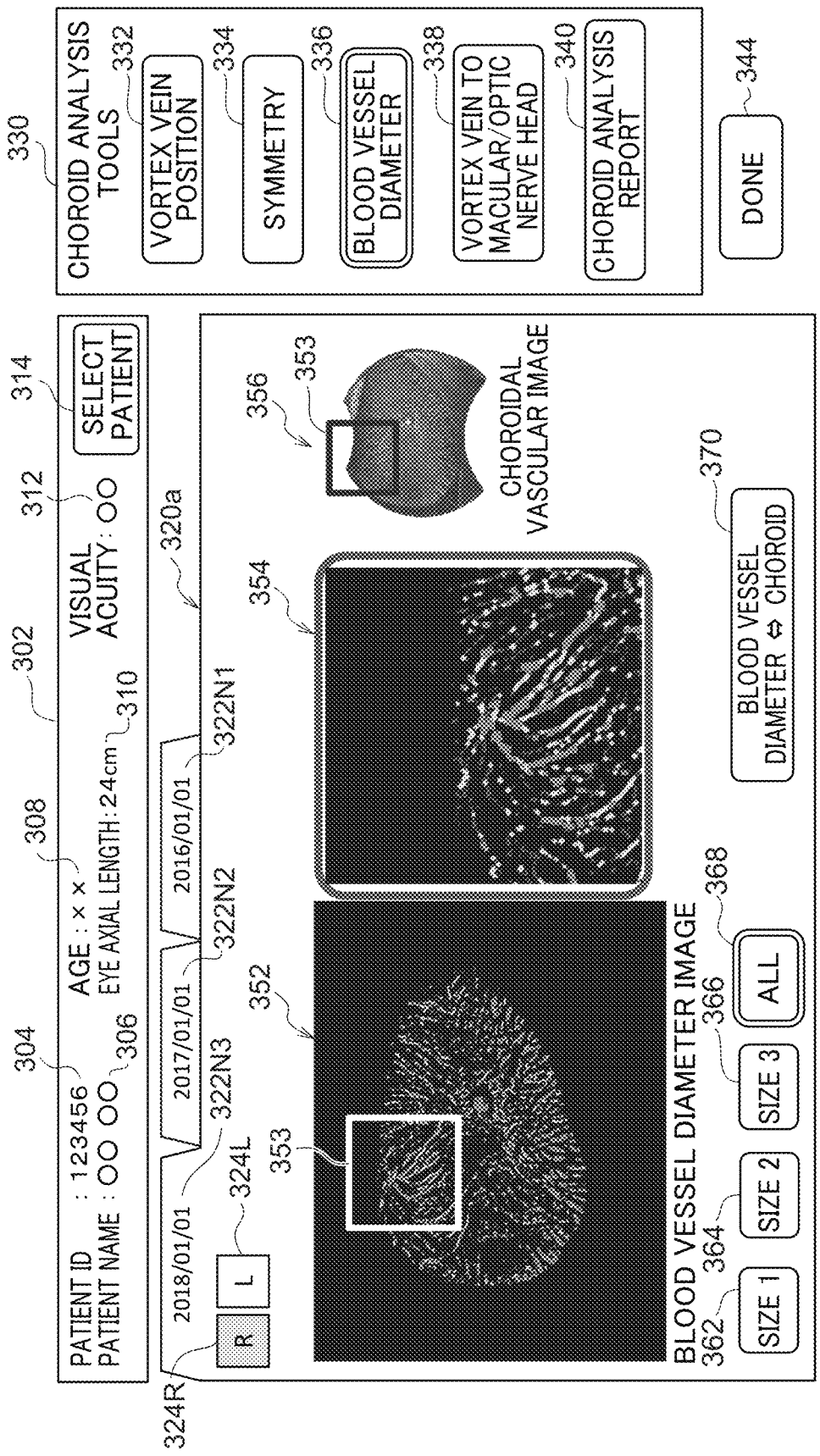
FIG. 11 is a diagram illustrating a display screen 300 including a display screen for displaying blood vessel diameters.

As illustrated in FIG. 11, the blood vessel diameter display screen 320a includes a colored blood vessel diameter image display field 352 for displaying a colored blood vessel diameter image, an enlarged image display field 354 for displaying an enlarged image of a portion of the colored blood vessel diameter image, and a contracted choroidal vascular image display field 356 for displaying a contracted choroidal vascular image.

When a region in the contracted choroidal vascular image display field 356, for example a rectangular region as illustrated in FIG. 11, is specified using a graphical user interface (hereafter referred to as GUI), the image viewer 150 displays a rectangular frame 353 around corresponding positions on the colored blood vessel diameter image display field 352, and displays an enlarged image of the specified region in the enlarged image display field 354.

Furthermore, in the image display field 320a there is also a size 1 icon 362, a size 2 icon 364, and a size 3 icon 366 provided for instructing display of images of the first size choroidal blood vessels, the second size choroidal blood vessels, or the third size choroidal blood vessels, respectively, and an ALL icon 368 provided for instructing display of an image of choroidal blood vessels of all sizes.

A blood vessel diameter ⇔ choroid icon 370 is a button to switch display contents between the colored blood vessel diameter image display field 352 and the contracted choroidal vascular image display field 356. When the blood vessel diameter ⇔ choroid icon 370 is clicked in the display state of FIG. 11, a choroidal fundus image is displayed in the colored blood vessel diameter image display field 352, and a contracted choroidal blood vessel image is displayed in the contracted choroidal vascular image display field 356. When the ALL icon 368 is clicked in FIG. 11, an image of choroidal blood vessels of all sizes is displayed in the colored blood vessel diameter image display field 352 and the enlarged image display field 354. Moreover, the example illustrated in FIG. 11 is an example in which the blood vessel diameter ⇔ choroid icon 370 has been clicked, and the blood vessel diameter image of the colored blood vessel diameter image display field 352 is displayed larger than the choroidal vascular image of the contracted choroidal vascular image display field 356.

When the size 1 icon 362 has been clicked, the first size blood vessel image containing only the first size blood vessels displayed in red is displayed in the colored blood vessel diameter image display field 352. When the size 2 icon 364 has been clicked, the second size blood vessel image containing only the second size blood vessels displayed in green is displayed in the colored blood vessel diameter image display field 352. When the size 3 icon 366 has been clicked, the third size blood vessel image containing only the third size blood vessels displayed in blue is displayed in the colored blood vessel diameter image display field 352.

Display screens, described later, of the image viewer 150 have icons and buttons for instructing generation of images, described later, displayed thereon. When the user of the image viewer 150 (an ophthalmologist or the like) clicks on one of the icons etc., an instruction signal corresponding to the clicked icon etc. is transmitted from the image viewer 150 to the management server 140. On receipt of the instruction signal from the image viewer 150, the management server 140 generates an image corresponding to the instruction signal, and transmits image data of the generated image to the image viewer 150. The image viewer 150 that has received the image data from the management server 140 then displays an image based on the received image data on the display. Display screen generation processing is performed in the management server 140 by a display screen generation program operated in the CPU 162.

Figure 12:
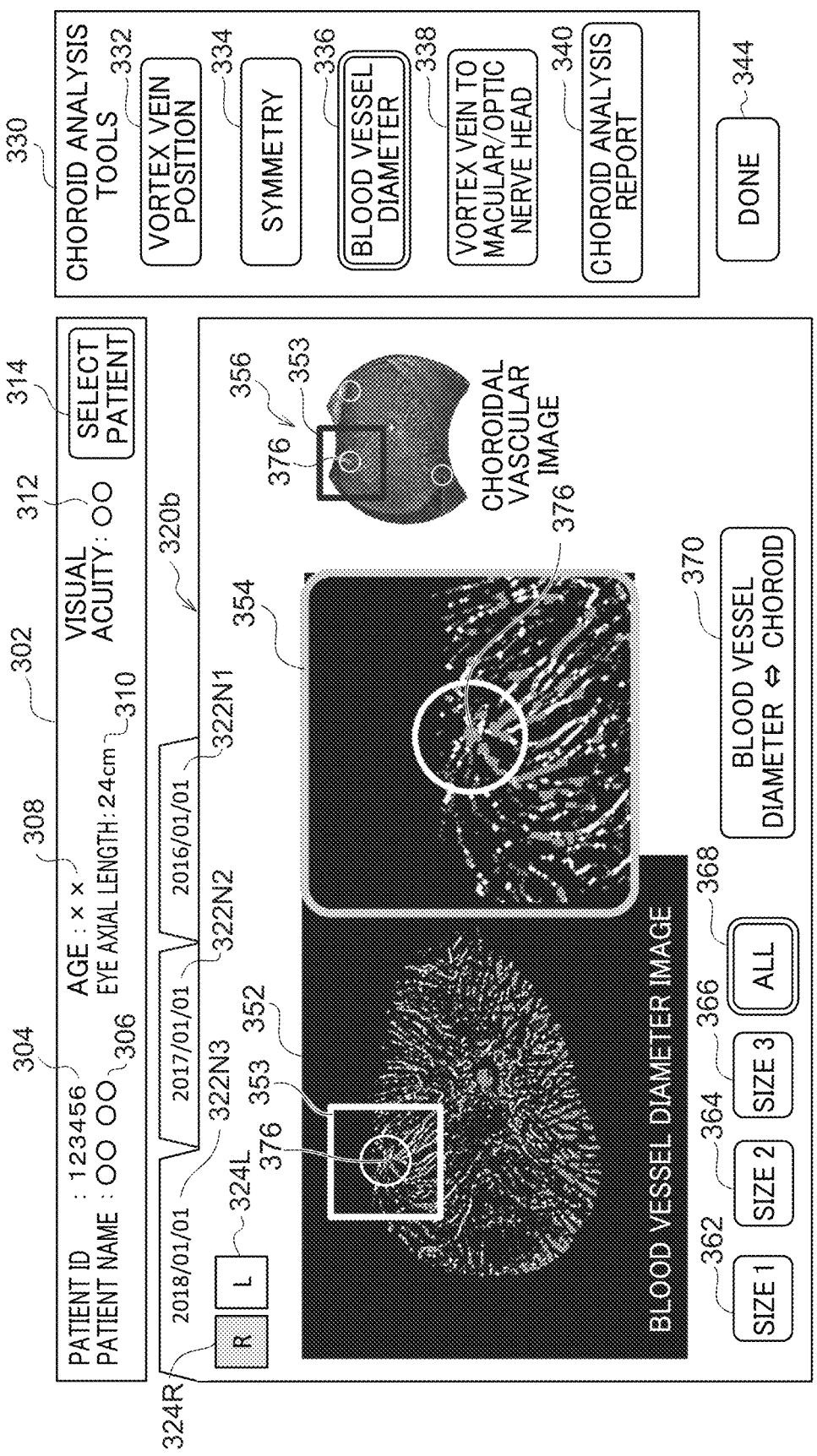
FIG. 12 is a diagram illustrating a display screen 300 with a VV position displayed superimposed on a display screen for displaying blood vessel diameters.
Figure 13:
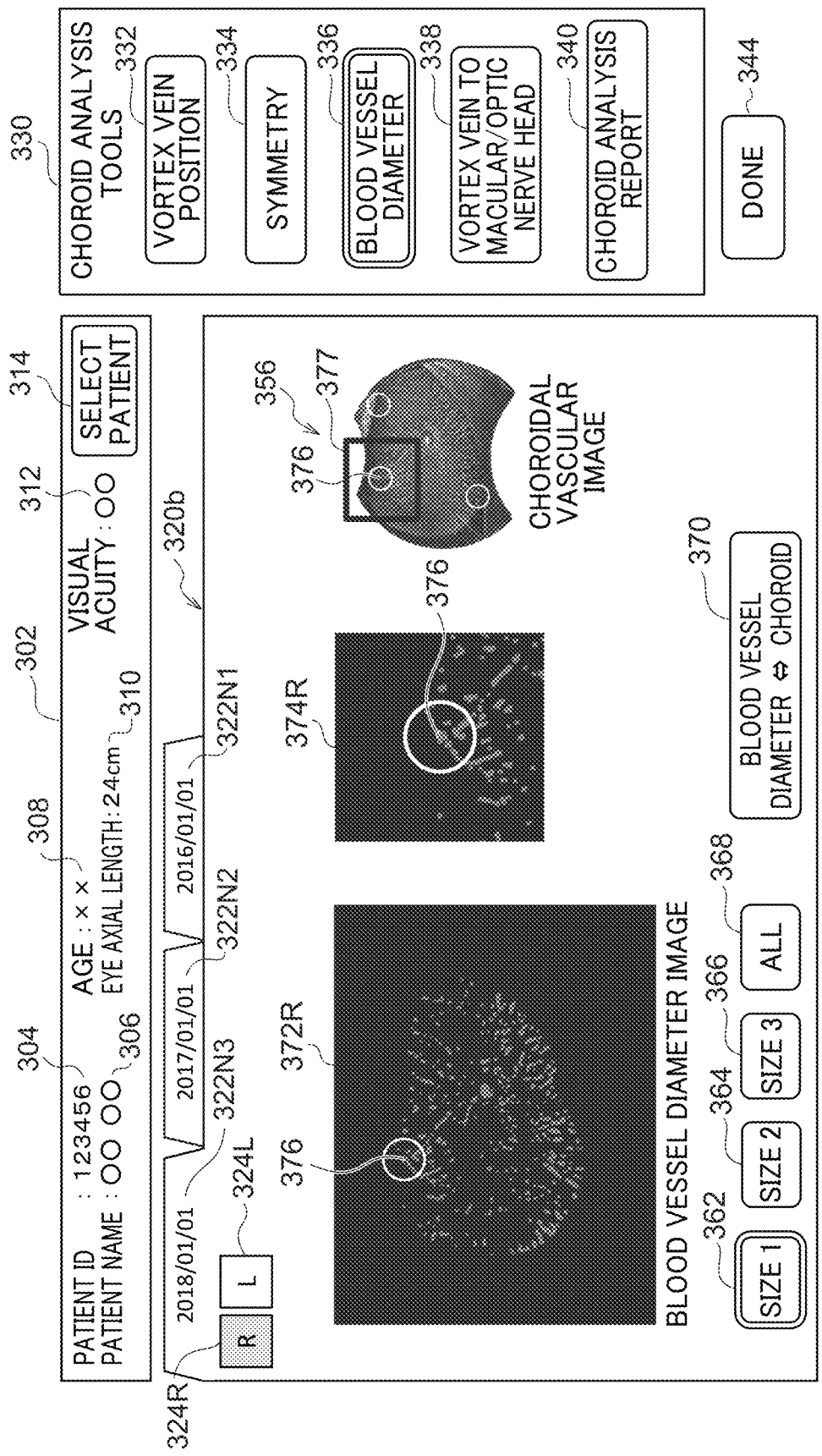
FIG. 13 is a diagram illustrating a display screen 300 displayed when a thickness 1 icon 362 is clicked.
Figure 14:
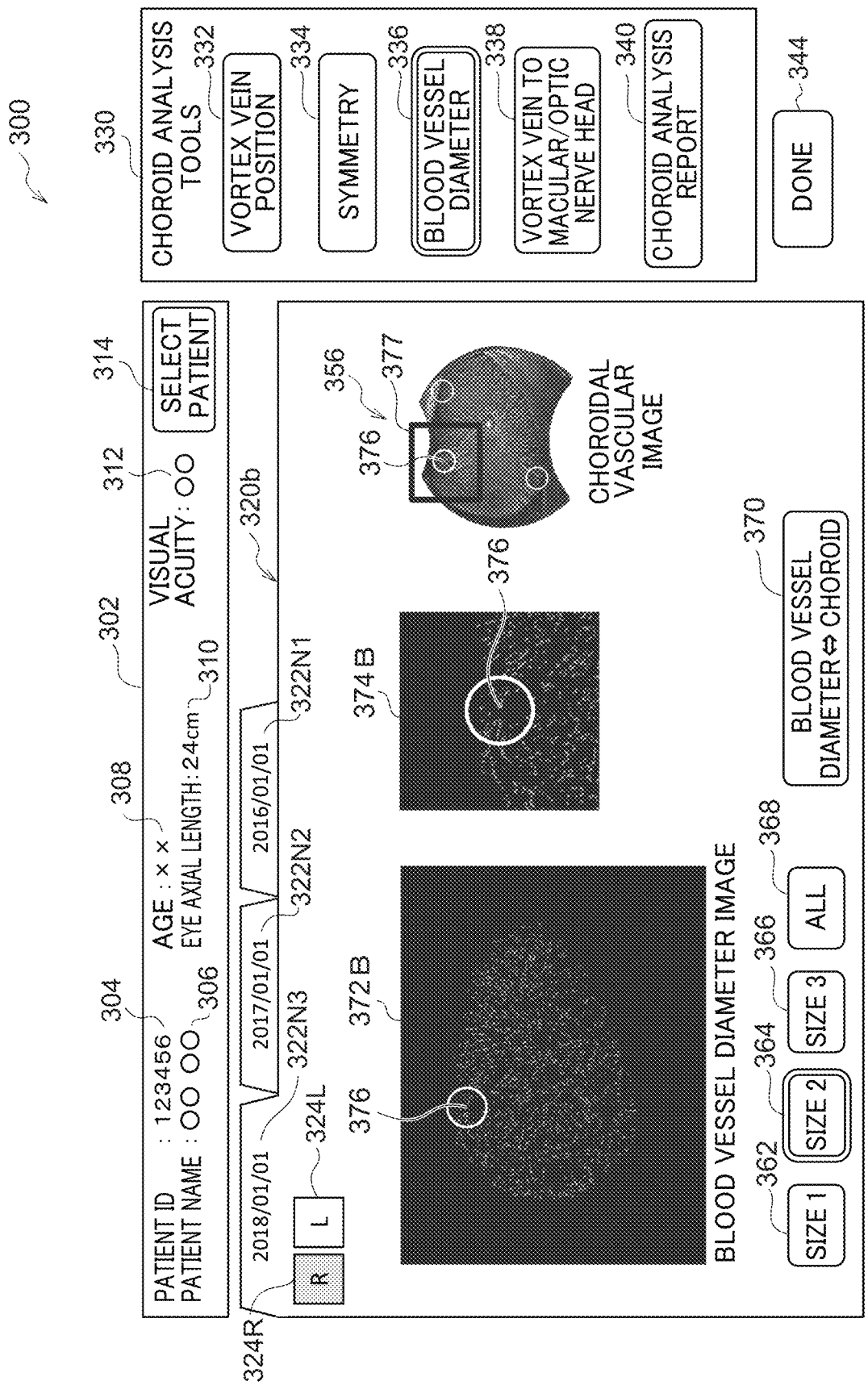
FIG. 14 is a diagram illustrating a display screen 300 displayed when a thickness 2 icon 364 is clicked.
Figure 15:
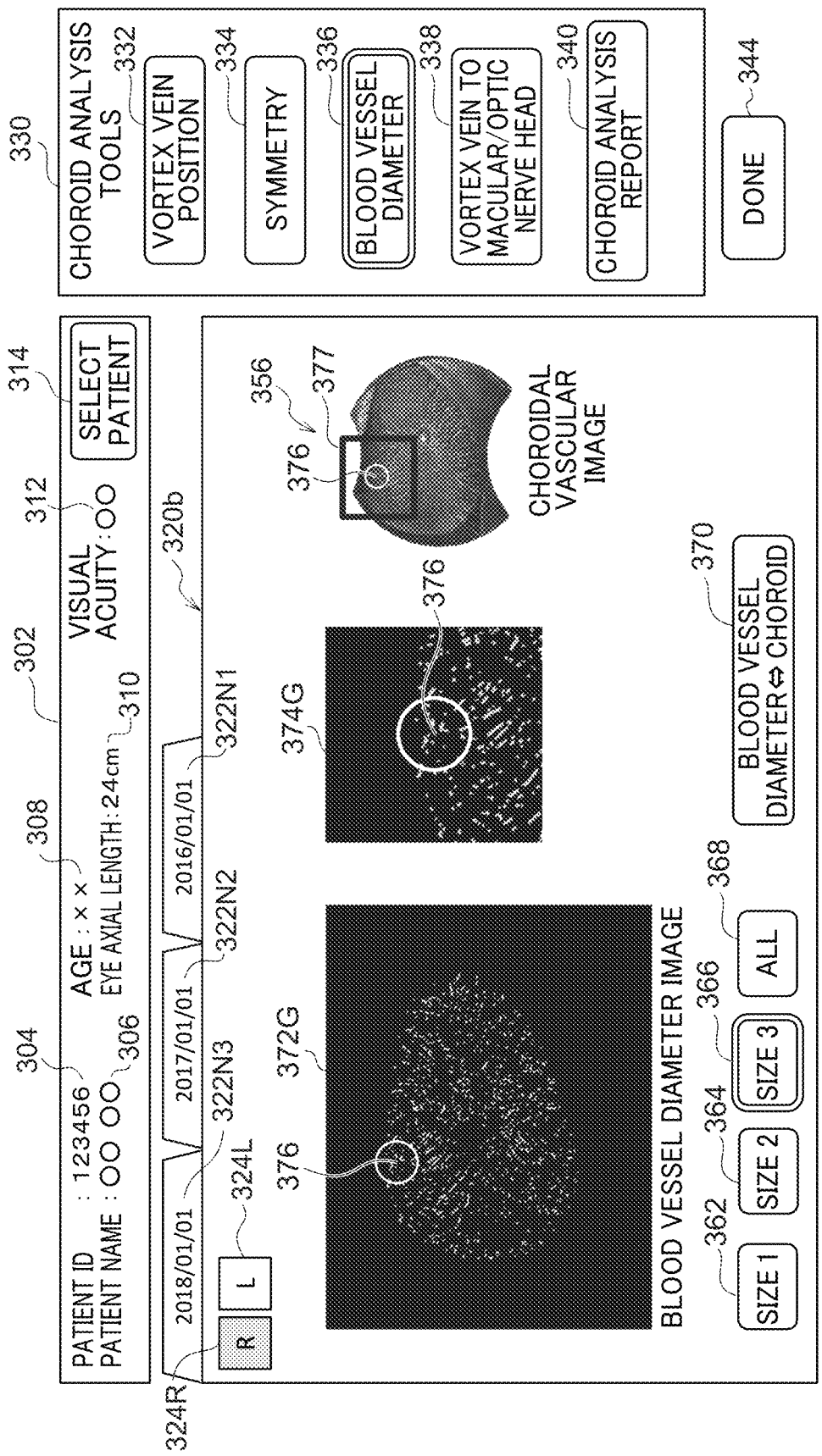
FIG. 15 is a diagram illustrating a display screen 300 displayed when a thickness 3 icon 366 is clicked.

Next, description follows regarding a second display embodiment for displaying the choroidal vascular analysis mode display screen on the image viewer 150. Similarly to the first display embodiment, the image viewer 150 displays the choroidal vascular analysis mode display screen 300 illustrated in FIG. 10 on the display 172 of the image viewer 150. When the blood vessel diameter icon 336 of the choroid analysis tool display field 330 in FIG. 10 is clicked, display changes to a display screen to display blood vessel diameters as illustrated in FIG. 12 (the image display field 320 of FIG. 10 is changed to the blood vessel diameter display screen 320b of FIG. 12). In the second display embodiment, the same reference numerals are appended to display contents the same as in the first display embodiment, and explanation thereof is omitted.

As illustrated in FIG. 12, the blood vessel diameter display screen 320b includes a colored blood vessel diameter image display field 352 for displaying a colored blood vessel diameter image, an enlarged image display field 354 for displaying an enlarged image of the colored blood vessel diameter image, and a contracted choroidal vascular image display field 356 for a choroidal vascular image in which positions of vortex veins (hereafter referred to as VV) are superimposed on the contracted choroidal vascular image. The VV position 376 is displayed as a circle on the choroidal vascular image displayed in the contracted choroidal vascular image display field 356. There are three VV positions illustrated by circles in FIG. 12.

The vortex veins VV are drains for blood that flowed into the choroid, with from four to six thereof being present on an equatorial portion of the eyeball toward the posterior pole of the eyeball. The VV positions are computed based on the running direction of the choroidal blood vessels.

The image viewer 150 receives data for the display screen 300 illustrated in FIG. 12 from the management server 140, and the management server 140 in turn executes a display screen data creation processing program illustrated in FIG. 24 to create the data for the display screen 300 illustrated in FIG. 12. Description follows regarding the display screen data creation processing program illustrated in FIG. 24.

At step 200, the processing section 186 reads the choroidal vascular image (see FIG. 6) from the memory 164.

At step 401, VV position detection processing is executed to detect the VV positions.

The VV position detection processing will now be described. The VV position detection processing is performed by analyzing the choroidal vascular image that was read at step 200. The image processing section 182 analyzes the VV positions in the following manner.

The image processing section 182 detects the running direction (blood vessel running direction) of each of the choroidal blood vessels in the choroidal vascular image. Specifically, first the image processing section 182 executes the following processing at each of the pixels in the choroidal vascular image. Namely, for a given pixel, the image processing section 182 sets a region (cell) centered on the given pixel, and then creates a histogram of brightness gradient directions at each pixel in the cell.

The brightness gradient direction is, for example, expressed as an angle from 0° to just under 180°. Note that 0° is defined as a direction of a straight line (horizontal line). Then in order to create a histogram with, for example, nine bins (with bin widths of 20°) of brightness gradient directions centered on 0°, 20°, 40°, 60°, 80°, 100°, 120°, 140°, and 160°, the image processing section 182 counts the number of pixels inside the cell having a gradient direction corresponding to each of the bins.

The width of a single bin in the histogram is 20°, and the 0° bin is set with the number (count value) of pixels in the cell having a gradient direction of from 0° up to but not including 10°, or a gradient direction of from 170° up to but not including 180°. The 20° bin is set with the number (count value) of pixels in the cell having a gradient direction of from 10° up to but not including 30°. The count values for the bins 40°, 60°, 80°, 100°, 120°, 140°, and 160° are set in a similar manner. Due to there being nine bins in the histogram, the blood vessel running direction at each of the pixels is defined as being in one of nine direction types. Note that the resolution of the blood vessel running direction can be raised by narrowing the width of each bin and increasing the number of bins. The count values of each of the bins (the vertical axis in the histogram) is normalized, and a histogram is created for each analysis point.

The image processing section 182 next takes the gradient direction of the bin having the smallest count in the histogram for each of the cells as the gradient direction for that pixel in each of the cells. This gradient direction corresponds to the blood vessel running direction. Note that the gradient direction having the smallest count is taken as the blood vessel running direction for the following reason. There is a small brightness gradient along the blood vessel running direction, however, there is a larger brightness gradient in other directions (for example, there is a large difference in brightness between blood vessels and tissue other than blood vessel). Thus when histograms of brightness gradient are created for each of the pixels, the count value is small for the blood vessel running direction. The blood vessel running direction is detected for each of the pixels in the choroidal vascular image by the processing described above.

The image processing section 182 sets initial positions for M (natural number)×N (natural number) (=L) individual imaginary particles. Specifically, the image processing section 182 sets the total of L individual initial positions across the choroidal vascular image, spaced uniformly with M imaginary particles in the vertical direction and N imaginary particles in the horizontal direction. Information about the detected blood vessel running directions is employed to estimate the positions of vortex veins VV by performing processing to move the imaginary particles across the choroidal vascular image in the blood vessel running directions. Due to the vortex veins VV being sites where there are plural choroidal blood vessel collected together, this is processing that utilizes the property that the plural imaginary particles arranged on the image follow the blood vessels to finally collect at the vortex vein positions.

The image processing section 182 estimates the VV positions. Specifically, the image processing section 182 performs the following processing on each of the L individual positions. Namely, the image processing section 182 acquires the blood vessel running direction of a first position (one of the L individual positions), moves this imaginary particle by a specific distance along the acquired blood vessel running direction, repeats acquisition of the blood vessel running direction but this time at the position moved to, and then moves this imaginary particle by the specific distance along this acquired blood vessel running direction. Such movements in this manner of a specific movement distance along the acquired blood vessel running direction are repeated a preset number of times. The above processing is executed for all of the L individual positions. At this point in time, a point where a given number of imaginary particles or more have collected together is taken as being a VV position.

VV position information (the number of VVs detected, coordinates on the choroidal vascular image, etc.) is stored in the memory 164. The VV position information is employed for FIG. 12 to FIG. 15, and to create the screen for a third exemplary embodiment of display screen for a choroidal vascular analysis mode of FIG. 22, described later.

At step 204, the image processing section 182 executes size analysis processing to analyze the size of choroidal blood vessels which appear as white in the binary image as described above.

At step 403, the image processing section 182 saves the VV positions and size analysis results in the memory 164. At step 405, the image processing section 182 creates a display screen (FIG. 12 or the like).

In this manner, the data for the display screen 300 illustrated in FIG. 12 is transmitted to the image viewer 150 from the management server 140, and in turn the management server 140 executes a display screen data creation processing program as illustrated in FIG. 12 and creates the data of the display screen 300 such as of FIG. 12 or the like. The management server 140 transmits the data of the display screen to the image viewer 150.

The VV position information (number of VVs, coordinates on the choroidal vascular image, etc.) is stored in the memory 164. The VV position information is employed for FIG. 12 to FIG. 15, and to create a screen of a third exemplary embodiment of a display screen for a choroidal vascular analysis mode of FIG. 22, described below.

When a VV region in the choroidal vascular image is desired for enlarged display in the contracted choroidal vascular image display field 356 is specified using a GUI, for example a rectangular region as illustrated in FIG. 12, the image viewer 150 displays the rectangular frame 353 at a corresponding position on the colored blood vessel diameter image display field 352, and displays a circle encircling the VV position 376 therein. An enlarged image of the specified VV region is displayed in the enlarged image display field 354. The VV position 376 and a circle encircling the periphery of the VV position 376 is displayed so as to be superimposed on the enlarged image.

In FIG. 12, the ALL icon 368 has been clicked, and an image of the choroid blood vessels of all sizes is displayed in the colored blood vessel diameter image display field 352 and in the enlarged image display field 354. In this state when, for example, the size 1 icon 362 is clicked, then the display contents of the colored blood vessel diameter image display field 352 and the enlarged image display field 354 changes to an image containing only the first size blood vessels, as illustrated in a blood vessel diameter image display field 372R and an enlarged image display field 374R of FIG. 13. Red is associated with the first size blood vessels, and so the first size blood vessels are displayed in red. When the size 2 icon 364 is clicked, the display contents of the colored blood vessel diameter image display field 352 and the enlarged image display field 354 changes to an image containing only the second size blood vessels, as illustrated in a blood vessel diameter image display field 372B and an enlarged image display field 374B of FIG. 14. Blue is associated with the second size blood vessels, and so the second size blood vessels are displayed in green. When the size 3 icon 366 is clicked, the display contents of the colored blood vessel diameter image display field 352 and the enlarged image display field 354 changes to an image containing only the third size blood vessels, as illustrated in a blood vessel diameter image display field 372G and an enlarged image display field 374G of FIG. 15. Green is associated with the third size blood vessels, and so the third size blood vessels are displayed in blue.

Next, description follows regarding the third display embodiment of display screen of a choroidal vascular analysis mode displayed on the image viewer 150. Similarly to the first display embodiment, the image viewer 150 displays the choroidal vascular analysis mode display screen 300 illustrated in FIG. 10 on the display 172 of the image viewer 150. When the blood vessel diameter icon 336 is clicked on the choroid analysis tool display field 330 of FIG. 10, display changes to a display screen combining blood vessel diameter analysis results and VV position analysis results as illustrated in FIG. 22 (the image display field 320 of FIG. 10 changes to the blood vessel diameter display screen 320c of FIG. 22).

Next, description follows regarding the third display embodiment of the choroidal vascular analysis mode display screen. The same reference numerals are appended to display contents in the third display embodiment the same as in the first display embodiment, and explanation thereof is omitted.

Figure 22:
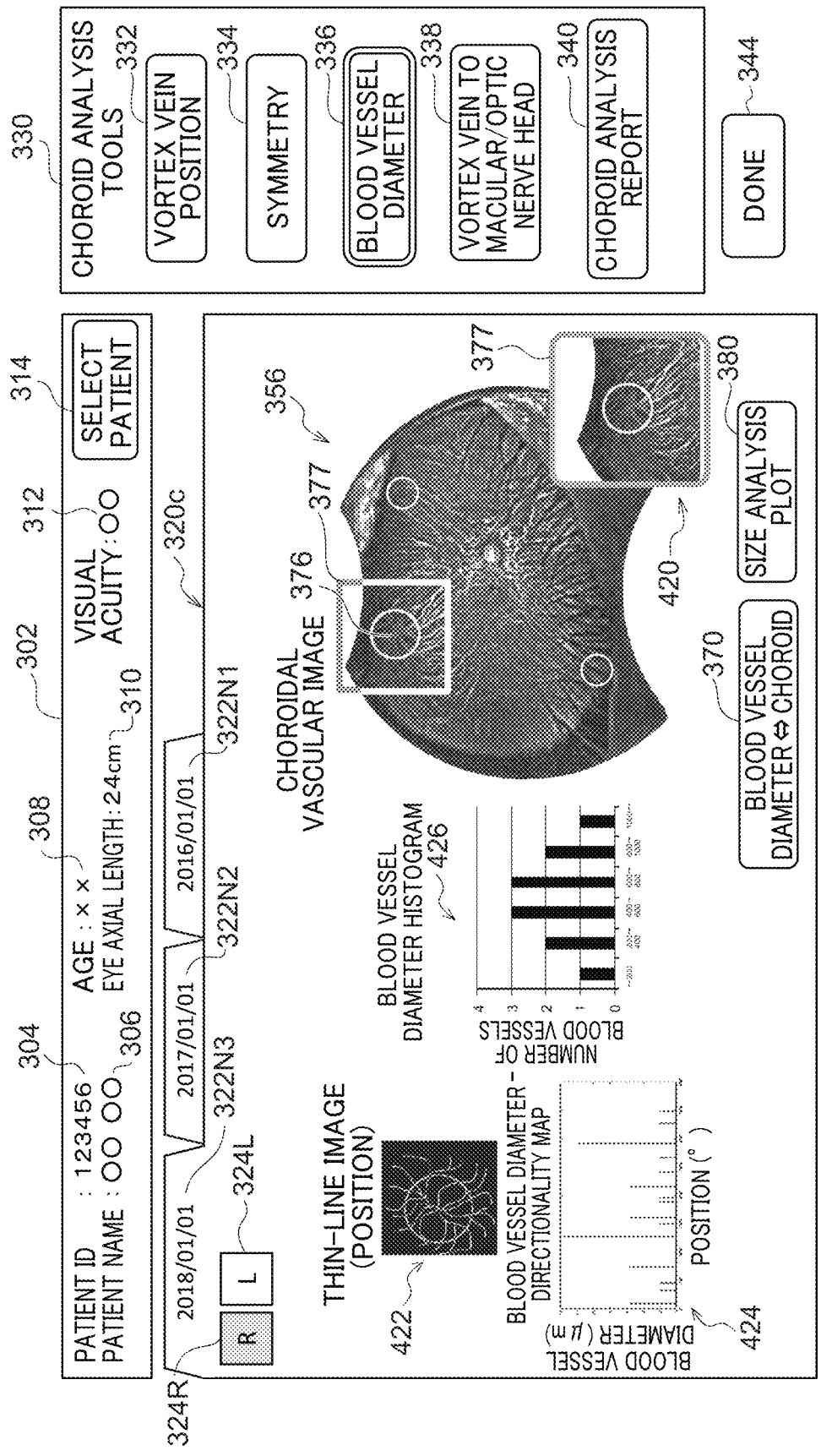
FIG. 22 is a diagram illustrating a display screen displaying various data about blood vessel diameter.

As illustrated in FIG. 22, in the blood vessel diameter display screen 320c, a choroidal vascular image is displayed with the VV position 376 displayed superimposed on the choroidal vascular image of the contracted choroidal vascular image display field 356. A circle of specific radius centered on the VV position is displayed on the choroidal vascular image of FIG. 22. Three VV positions are indicated by circles in FIG. 12.

The blood vessel diameter display screen 320c further includes display fields to display a VV position enlarged image 420, a VV thin-line image 422, a VV blood vessel diameter-directionality map 424, a blood vessel diameter histogram 426, and a size analysis plot icon 380. The size analysis plot icon 380 is a button to switch the display contents to the display screen of FIG. 23, described later.

When a VV position is specified using a GUI, a rectangular frame 377 is displayed in the contracted choroidal vascular image display field 356 of the choroidal vascular image so as to surround a circle at the specified VV position. The VV position enlarged image 420 of the rectangular frame 377 is then displayed in the display field. The VV position enlarged image 420 created and displayed uses data from detailed analysis of the choroidal blood vessels at the periphery of the specified VV. The VV blood vessel diameter-directionality map 424 created in a similar manner is displayed in a VV blood vessel diameter-directionality map display field.

Figure 16:
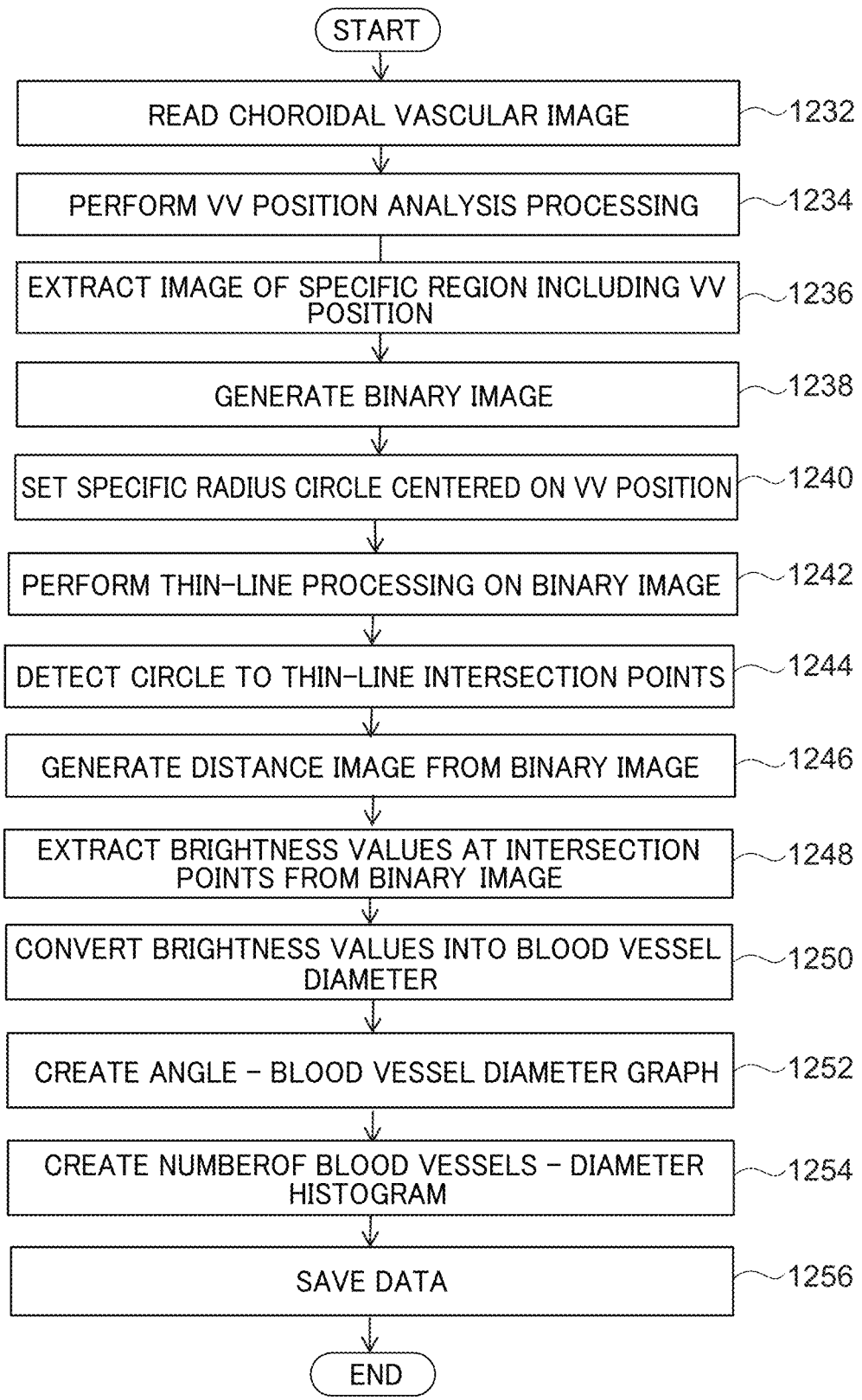
FIG. 16 is a flowchart of an image processing program of a fourth exemplary embodiment.

Detailed description next follows regarding a creation processing method (image processing program) for the VV thin-line image 422 and the VV blood vessel diameter-directionality map 424, with reference to FIG. 16. The image processing program illustrated in FIG. 16 is, similarly to the program of FIG. 5, executed when a choroidal vascular image is generated based on the fundus images.

At step 1232 of FIG. 16, the processing section 186 reads the choroidal vascular image (see FIG. 6), at step 1234, the image processing section 182 executes the VV position analysis processing described above.

At step 1236, the image processing section 182 extracts an image of a specific region containing a VV position in the choroidal vascular image.

Figure 17:
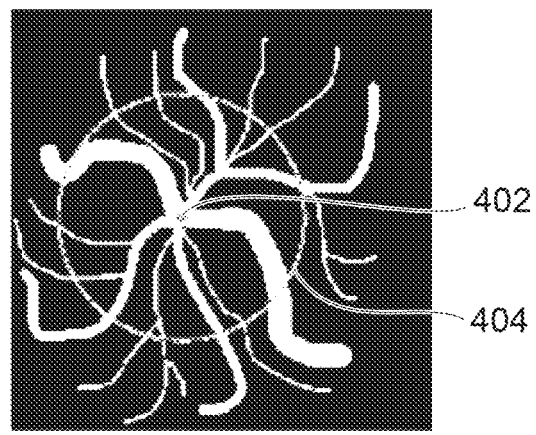
FIG. 17 is a diagram in which a specific radius circle 404 has been set centered on a VV position 402 in a binary image generated from a choroidal vascular image.

At step 1238, the image processing section 182 generates a binary image from the extracted specific region image. At step 1240, the image processing section 182 sets a circle 404 of a specific radius centered on the VV position 402 in the generated binary image, as illustrated in FIG. 17. The specific radius of the circle 404 is 6 mm. However, depending to the analysis required, the radius of the circle 404 may be set so as to be from 2 mm to 20 mm. A configuration may also be adopted such that the radius of the circle 404 is set based on a pattern of blood vessel tracks at the periphery of the VV position.

Figure 18:
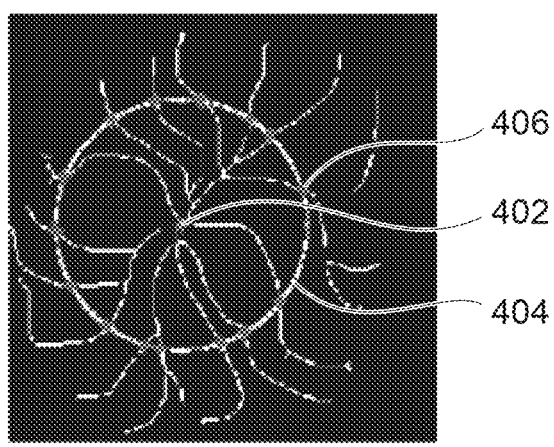
FIG. 18 is a diagram of intersection points 406 detected between thin-lines and the circle 404.
Figure 19:
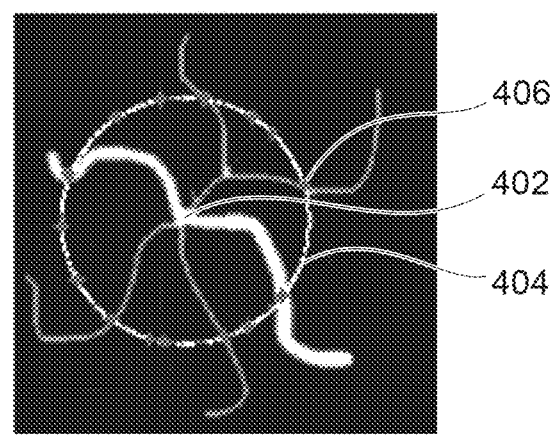
FIG. 19 is a diagram illustrating a distance image generated from the binary image of the choroidal vascular image.

At step 1242, the image processing section 182 performs thin-line processing on the binary image. At step 1244, the image processing section 182 detects intersection points 406 between thin-lines and the circle 404, as illustrated in FIG. 18. At step 1246, the image processing section 182 generates a distance image as illustrated in FIG. 19 from the binary image. The distance image is an image in which, according to the thickness of line in the binary image, the brightness of a line is gradually brighter on progression from edges of the line toward the center thereof, with the brightness of positions at the center of lines being brighter as the line thickness becomes thicker.

At step 1248, the image processing section 182 extracts brightness values of positions corresponding to each of the intersection points 406 from the distance image. At step 1250, the image processing section 182 converts brightness values at each of the intersection points 406 into a blood vessel diameter according to a look up table that is stored in the memory 164 and that indicates correspondence relationships between pixel brightness and blood vessel diameter.

Figure 20:
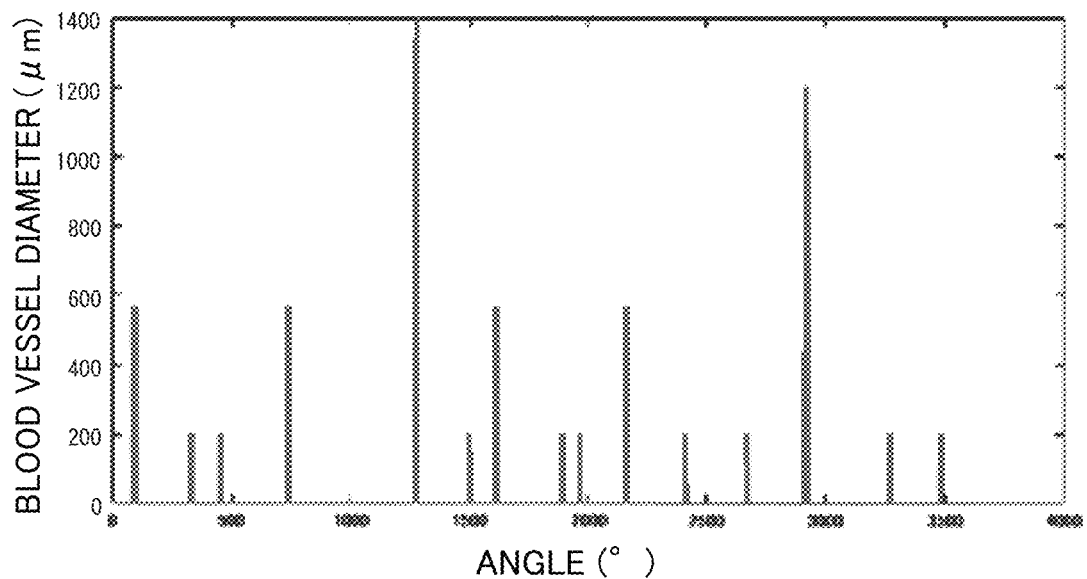
FIG. 20 is a graph of blood vessel diameter against angle from an uppermost edge of the circle.

At step 1252, the display control section 184 creates a graph as illustrated in FIG. 20 in which an angle from a specific position (for example, the uppermost edge) of a circle through the intersection points 406 positions is plotted on the horizontal axis, and the blood vessel diameter at each intersection point 406 is plotted on the vertical axis. This graph enables a visualization of the size of blood vessels tracking out from the VV position 402 against blood vessel running direction.

Figure 21:
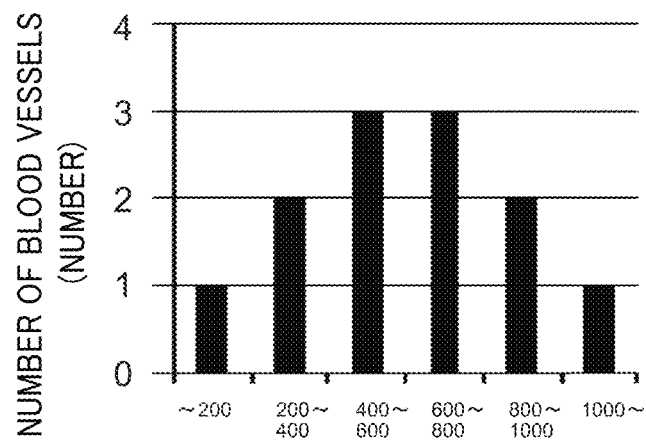
FIG. 21 is a histogram of number of choroidal blood vessels against blood vessel diameter.

At step 1254, as illustrated in FIG. 21, the display control section 184 tallies the blood vessel diameters at the intersection points 406, and creates a histogram of the number of choroidal blood vessels against blood vessel diameter for six bins having bin widths of 200 µm. A size distribution of blood vessels connected to a VV can be visualized from this histogram, enabling the flow rate etc. of blood flowing into the VV to be estimated.

At step 1256, the processing section 186 saves the following data. The various data saved in the memory 164 includes data related to the VV position, the binary image, the circle 404 of a specific radius centered on the VV position 402, the intersection points 406 between thin-lines and the circle 404, the distance image, the brightness values at positions corresponding to each of the intersection points 406, the blood vessel diameters converted from the brightness values of each of the intersection points 406, the graph of blood vessel diameter against angle, and the histogram of number of choroidal blood vessels against blood vessel diameter.

Next, description follows regarding a fourth display embodiment of choroidal vascular analysis mode display screen displayed on the image viewer 150 when the size analysis plot icon 380 of FIG. 22 is clicked. When the size analysis plot icon 380 of FIG. 22 is clicked, the display screen is changed to a display screen combining blood vessel diameter analysis results and VV position analysis results as illustrated in FIG. 23 (the image display screen field 320c of FIG. 22 is changed to an image display screen field 320d of FIG. 23). In the fourth display embodiment, the same reference numerals are appended to portions of the display embodiment the same as in the first display embodiment, and explanation thereof is omitted.

Next, description follows regarding the image display screen field 320d of FIG. 23. A colored choroidal vascular image 500 is displayed at the center of the image display screen field 320d, with positions of vortex veins (VV) superimposed thereon. In FIG. 23, there are four VVs present: a VV 520 at the top left of the colored choroidal vascular image 500, a VV 540 at the bottom left thereof, a VV 560 at the top right thereof, and a VV 580 at the bottom right thereof.

A circle 522 of specific radius centered on the VV 520 is also displayed superimposed on the colored choroidal vascular image 500. For the other VVs, circles 542, 562, 582 are also similarly displayed superimposed thereon.

Moreover, an enlarged-circle display image 524, and a pie chart 526 are also displayed at the left top of the image display screen field 320*d*. The enlarged-circle display image 524 is an enlarged display image of a colored choroidal vascular image of an area encircled by the circle 522. The pie chart 526 indicates proportions of the number of pixels in blood vessel regions occupied by blood vessels for each of plural sizes, with respect to a total number of pixels of the blood vessel regions inside the circle 522 taken as 100. Specifically, for example, the pie chart 526 firstly includes a proportion of the number of pixels of the region occupied by the first size (480 µm or greater) blood vessels i.e. occupied by large blood vessels, secondly a proportion of the number of pixels of the region occupied by the second size (from 320 µm up to but not including 480 µm) blood vessels i.e. occupied by medium blood vessels, and thirdly a proportion of the number of pixels of the region occupied by the third size (less than 320 µm) blood vessels i.e. occupied by fine blood vessels. Similarly, an enlarged-circle display image 544 and a pie chart 546 are displayed at the bottom left of the image display screen field 320*d*, an enlarged-circle display image 564 and a pie chart 566 are displayed at the top right of the image display screen field 320*d*, an enlarged-circle display image 564 and a pie chart 566 are displayed at the top right of the image display screen field 320*d*, and an enlarged-circle display image 584 and a pie chart 586 are displayed at the bottom right of the image display screen field 320*d*.

Each of the images displayed in the image display screen field 320*d* is created by the image processing section 182 of the management server 140.

The fourth display embodiment enables a user such as an ophthalmologist to ascertain the positions of all the VVs on the display screen, and to ascertain the overall distribution of blood vessel sizes in the enlarged images at each of the VVs.

In each of the exemplary embodiments described above, the choroidal blood vessels are extracted from the fundus images and the sizes of the choroidal blood vessels are determined therefrom.

Hitherto although the choroid vascular plexus has been quantified from OCT measurement data, the ascertaining of sizes thereof has not been possible. However, in each of the exemplary embodiments described above, the retinal blood vessels and the choroidal blood vessels are separated from the first fundus image (R fundus image) or IR fundus image and the second fundus image (G fundus image), the sizes of the choroidal blood vessels determined, and the determined sizes are visualized by displaying in different colors. This enables the sizes of the choroidal blood vessels to be ascertained.

Furthermore, the sizes of the choroidal blood vessels at the vortex vein VV position periphery is analyzed and visualized, enabling diagnostic support to be given to an ophthalmologist.

The exemplary embodiments described above enable the VV positions to be analyzed, and the size of the choroidal blood vessels at the VV periphery to be analyzed.

The exemplary embodiments described above also hold position information for each size of choroidal blood vessel, enabling statistical processing to be performed easily.

In the exemplary embodiments described above the fundus region is imaged over a wide range of approximately 120° of external light illumination angle from outside the examined eye 12 (which equates to an internal light illumination angle of about 200°), enabling the choroid to be visualized over a wide range of the fundus. Thus not only can the size of the choroidal blood vessels be analyzed in a peripheral region of the fundus, but the sizes of the choroidal blood vessels at the periphery of the vortex veins VV present in the vicinity of the equator of the eyeball can also be analyzed.

Next, description follows regarding various modified examples of the technology disclosed herein.

First Modified Example

Although in each of the exemplary embodiments described above the choroidal vascular image is analyzed, the technology disclosed herein is not limited thereto. Images that may be analyzed include, for example, OCT-en face images (fundus images constructed from 3D OCT data), images obtained using indocyanine green (ICG) fluoroscopy methods, images obtained using fluorescein angiography (FA), images of fundus sections obtained using fundus autofluorescence (FAF), and the like.

Second Modified Example

Although in each of the exemplary embodiments described above the choroidal blood vessels are displayed with colors that vary according to size, the technology disclosed herein is not limited thereto, and the choroidal blood vessels may be displayed with brightness values that vary according to size.

Third Modified Example

In the above exemplary embodiments, the management server 140 executes the image processing program in advance, the technology disclosed herein is not limited thereto. For example, the following configuration may be adopted. For example, the management server 140 may execute the image processing program when the blood vessel diameter icon 336 is clicked in a state in which the choroidal vascular analysis mode display screen 300 illustrated in FIG. 10 is being displayed on the display 172 of the image viewer 150. Specifically, the image viewer 150 may transmit a command to the management server 140 when the blood vessel diameter icon 336 has been clicked. The management server 140 may then be configured so as to execute the image processing program on receipt of this command.

Fourth Modified Example

In the exemplary embodiments described above examples have been described in which a fundus image is acquired by the ophthalmic device 110 with an internal light illumination angle of about 200 degrees. However, the technology disclosed herein is not limited thereto, and the technology disclosed herein may be applied even when the fundus image has been imaged by an ophthalmic device with an internal illumination angle of 100 degrees or less, and may also be applied to a montage image obtained by combining plural fundus images.

Fifth Modified Example

In the exemplary embodiments described above the fundus image is imaged by the ophthalmic device 110 equipped with an SLO imaging unit. However, the technology disclosed herein may be applied to a fundus image by a fundus camera capable of imaging choroidal blood vessels, and to images obtained by OCT angiography.

Sixth Modified Example

In the exemplary embodiments described above, the image processing program is executed by the management server 140. However the technology disclosed herein is not limited thereto. For example, the image processing program may be executed by the ophthalmic device 110 or the image viewer 150. In cases in which the ophthalmic device 110 executes the image processing program, the image processing program is stored in the memory 24. Moreover, in cases in which the image processing program is executed by the image viewer 150, the image processing program is stored in the memory 164 of the image viewer 150.

Seventh Modified Example

The exemplary embodiments described above describe an example of the ophthalmic system 100 equipped with the ophthalmic device 110, the eye axial length measuring instrument 120, the management server 140, and the image viewer 150, however the technology disclosed herein is not limited thereto. For example, as a first example, the eye axial length measuring instrument 120 may be omitted, and the ophthalmic device 110 may be configured so as to further include the functionality of the eye axial length measuring instrument 120. Moreover, as a second example, the ophthalmic device 110 may be configured so as to further include the functionality of one or both of the management server 140 and the image viewer 150. For example, the management server 140 may be omitted in cases in which the ophthalmic device 110 includes the functionality of the management server 140. In such cases, the image processing program is executed by the ophthalmic device 110 or the image viewer 150. Moreover, the image viewer 150 may be omitted in cases in which the ophthalmic device 110 includes the functionality of the image viewer 150. As a third example, the management server 140 may be omitted, and the image viewer 150 may be configured so as to execute the functionality of the management server 140.

OTHER MODIFIED EXAMPLES

The data processing described in the exemplary embodiments described above is merely an example thereof. Obviously, unnecessary steps may be omitted, new steps may be added, and the sequence of processing may be changed within a range not departing from the spirit thereof.

Moreover, although in the exemplary embodiments described above an example has been given of a case in which data processing is implemented by a software configuration utilizing a computer, the technology disclosed herein is not limited thereto. For example, instead of a software configuration utilizing a computer, the data processing may be executed solely by a hardware configuration of FPGAs or ASICs. Alternatively, a portion of processing in the data processing may be executed by a software configuration, and the remaining processing may be executed by a hardware configuration.

What is claimed is:

1. An image processing method comprising:
   detecting a vortex vein position from a fundus image in which choroidal blood vessels have been visualized;
   analyzing a size of the choroidal blood vessels in the fundus image; and
   creating a display screen indicating a relationship between the vortex vein position and size of the choroidal blood vessel.

2. The image processing method according to claim 1, wherein the display screen is a screen showing analysis information obtained by analyzing the size of a choroidal blood vessel included in a predetermined range including the vortex vein position.

3. The image processing method according to claim 1, wherein the vortex vein position is the position of the vortex vein selected by the user from the plurality of vortex veins specified in the fundus image.

4. The image processing method of claim 1, further comprising outputting image data of the display screen.

5. The image processing method of claim 1, wherein the display screen includes a vortex vein position overlaid fundus image in which the vortex vein position is overlaid.

6. The image processing method of claim 1, wherein the size of the choroidal blood vessels is a thickness of the choroidal blood vessels.

7. The image processing method of claim 1, wherein the size of the choroidal blood vessels is a diameter of the choroidal blood vessels.

8. The image processing method of claim 1, wherein the display screen includes a choroidal blood vessels image in which the choroidal blood vessels have been visualized as a result of analyzing the size of the choroidal blood vessels.

9. The image processing method of claim 1, wherein analyzing the size of the choroidal blood vessels in the fundus image includes extracting, by performing an image processing on the fundus image, a first size choroidal blood vessel with a first size and a second size choroidal blood vessel with a second size that is different from the first size.

10. The image processing method of claim 9, wherein analyzing the size of the choroidal blood vessels in the fundus image includes extracting the first size choroidal blood vessel by performing a first contraction processing on a binary image generated based on the fundus image, and extracting the second size choroidal blood vessel by performing a second contraction processing, which performs different pixel contraction than the first contraction processing, on the binary image.

11. The image processing method of claim 9, wherein the display screen includes a size analysis fundus image that displays the first size choroidal blood vessel by a first display method and the second size choroidal blood vessel by a second display method that is different from the first display method.

12. The image processing method of claim 1, wherein a plurality of vortex vein positions are detected in the vortex vein position detecting step.

13. The image processing method of claim 1, wherein analyzing the size of the choroidal blood vessel in the fundus image includes:
   detecting intersection points between choroidal blood vessels and a circle centered on the vortex vein position; and identifying the size of the choroidal blood vessels at the intersection points.

14. The image processing method of claim 13, wherein analyzing the size of the choroidal blood vessel in the fundus image further includes creating a graph indicating a relationship between a position on the circle of the intersection point and the size of the choroidal blood vessel at the intersection point.

15. The image processing method of claim 14, wherein analyzing the size of the choroidal blood vessel in the fundus image further includes creating a histogram of a number of the choroidal blood vessels against the blood vessel diameter.

16. A non-transitory computer-readable mediums storing a program to cause a computer to execute an image processing method comprising:
   detecting a vortex vein position from a fundus image in which choroidal blood vessels have been visualized;
   analyzing a size of the choroidal blood vessels in the fundus image; and
   creating a display screen indicating a relationship between the vortex vein position and size of the choroidal blood vessel.

17. An image processing device comprising:
a storage device configured to store a program to cause an image processing method to be executed by a processing device; and
a processing device configured to execute the image processing method by executing the program stored in the storage device, wherein
the image processing method comprises:
   detecting a vortex vein position from a fundus image in which choroidal blood vessels have been visualized;
   analyzing a size of the choroidal blood vessels in the fundus image; and
   creating a display screen indicating a relationship between the vortex vein position and size of the choroidal blood vessel.

* * * * *